United States Patent
Nakatsugawa et al.

(10) Patent No.: US 8,431,902 B2
(45) Date of Patent: Apr. 30, 2013

(54) RADIOGRAPHIC IMAGING DEVICE

(71) Applicant: Fujifilm Corporation, Tokyo (JP)

(72) Inventors: Haruyasu Nakatsugawa, Kanagawa (JP); Naoyuki Nishinou, Kanagawa (JP); Yasunori Ohta, Kanagawa (JP); Toshitaka Agano, Kanagawa (JP); Fumito Nariyuki, Kanagawa (JP); Naoto Iwakiri, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/685,725

(22) Filed: Nov. 27, 2012

(65) Prior Publication Data

US 2013/0082184 A1    Apr. 4, 2013

Related U.S. Application Data

(63) Continuation of application No. PCT/JP2011/062270, filed on May 27, 2011.

(30) Foreign Application Priority Data

May 31, 2010 (JP) ................................ 2010-125313
Nov. 4, 2010 (JP) ................................ 2010-247824
May 13, 2011 (JP) ................................ 2011-108447

(51) Int. Cl.
  *G01T 1/20*    (2006.01)
(52) U.S. Cl.
  USPC ...................................... 250/361 R; 250/366
(58) Field of Classification Search ............... 250/361 R, 250/366, 370.08, 370.09, 370.11; 378/4, 378/5, 16, 62
See application file for complete search history.

(56) References Cited

U.S. PATENT DOCUMENTS

| | | | | |
|---|---|---|---|---|
| 7,847,258 B2* | 12/2010 | Yaegashi et al. | ......... | 250/370.08 |
| 2008/0054183 A1* | 3/2008 | Nagata et al. | ............ | 250/370.11 |
| 2008/0099687 A1* | 5/2008 | Shoji et al. | ..................... | 250/368 |
| 2009/0026379 A1* | 1/2009 | Yaegashi et al. | ......... | 250/370.09 |
| 2012/0312998 A1* | 12/2012 | Osawa et al. | .................. | 250/366 |

FOREIGN PATENT DOCUMENTS

| | | | |
|---|---|---|---|
| JP | 2002-168806 A | 6/2002 |
| JP | 2009-32854 A | 2/2009 |
| JP | 2009-212377 A | 9/2009 |
| JP | 2010-66137 A | 3/2010 |
| WO | 2009/051017 A1 | 4/2009 |

OTHER PUBLICATIONS

"Research Regarding Anti-Radiation Characteristics of the Zinc Oxide Series Electronic Device", Open Joint Research Report of the Wakasa Wan Energy Research Center for 2009, Mar. 2010.

(Continued)

*Primary Examiner* — Mark R Gaworecki
(74) *Attorney, Agent, or Firm* — SOLARIS Intellectual Property Group, PLLC

(57) ABSTRACT

The present invention provides a radiographic imaging device that may image radiographic images with high sharpness while suppressing a drop in sensitivity. Namely, a radiation detector, in which a scintillator that generates light due to irradiation of radiation and a TFT substrate on which plural sensor portions configured including an organic photoelectric conversion material that generates electric charges by receiving light are disposed are sequentially layered, is positioned in such a way that radiation that has passed through a subject is made incident from the TFT substrate side.

9 Claims, 27 Drawing Sheets

OTHER PUBLICATIONS

Written Opinion of the ISA issued in International Application No. PCT/JP2011/062270 on Jun. 21, 2011.

International Search Report issued in International Application No. PCT/JP2011/062270 on Jun. 21, 2011.

* cited by examiner

RADIOGRAPHIC IMAGING DEVICE

CROSS-REFERENCE TO RELATED APPLICATIONS

This application is a continuation application of International Application No. PCT/JP2011/062270, filed on May 27, 2012, which is incorporated herein by reference. Further, this application claims priority from Japanese Patent Application No. 2010-125313, filed on May 31, 2010, Japanese Patent Application No. 2010-247824, filed on Nov. 4, 2010, and Japanese Patent Application No. 2011-108447, filed on May 13, 2012.

TECHNICAL FIELD

The present invention relates to a radiographic imaging device.

BACKGROUND ART

In recent years, radiation detectors such as flat panel detectors (FPD), in which a radiation sensitive layer is positioned on a thin-film transistor (TFT) active matrix substrate and which may directly convert radiation such as X-rays into digital data, have been put into practical use. Radiographic imaging devices using these radiation detectors have the advantage that, compared to conventional radiographic imaging devices using X-ray film or imaging plates, images may be checked instantly, and fluoroscopy, which continuously images radiographic images (images moving images), may also be performed.

Various types of this kind of radiation detector have been proposed; for example, there is the indirect-conversion-type, in which the radiation is first converted into light by a CsI:Tl, GOS ($Gd_2O_2S$:Tb), or other scintillator and then the light, into which the radiation has been converted, is converted into electric charges by sensor portions such as photodiodes and the electric charges are stored. The radiographic imaging device reads out, as electrical signals, the electric charges that have been stored in the radiation detector, uses amplifiers to amplify the electrical signals that have been read out, and thereafter uses analog-to-digital (A/D) conversion sections to convert the electrical signals into digital data.

As a technology relating to this kind of radiation detector, in JP-A No. 2002-168806, there is disclosed a technology in which the radiation detector is positioned in such a way that radiation that has passed through a subject is made incident from the scintillator side, part of the side of the scintillator to which the radiation is irradiated is covered by a mask member comprising a material that does not pass through the radiation, and the degree of deterioration of the radiation detector is determined by comparing the dark current that is output from the photodiodes in the region covered by the mask member and the dark current that is output from the photodiodes in the region not covered by the mask member.

Further, in JP-A No. 2009-32854, there is described a radiation detector in which the sensor portions are formed by an organic photoelectric conversion material.

DISCLOSURE OF INVENTION

Technical Problem

Incidentally, radiation may be irradiated to a radiation detector from the front side on which the scintillator is disposed (front side irradiation) or from the substrate side (back side) (back side irradiation).

In a case where the radiation detector is back-side irradiated, an image with high sharpness may be obtained because the light emission by the scintillator is close to the substrate, but sensitivity drops because absorption of the radiation occurs in the substrate when the radiation passes through the substrate.

In a case where the radiation detector is front-side irradiated, a drop in sensitivity does not occur because there is no absorption of the radiation by the substrate, but the sharpness of the obtained image becomes lower, because the thicker the scintillator becomes, the more the light emission by the scintillator is away from the substrate.

The present invention provides a radiographic imaging device that may image radiographic images with high sharpness while suppressing a drop in sensitivity.

Solution to Problem

A radiographic imaging device according to a first aspect of the invention includes a radiation detector, in which a light-emitting layer that generates light due to irradiation of radiation and a substrate on which plural sensor portions configured including an organic photoelectric conversion material that generates electric charges by receiving light are disposed and are sequentially layered, with the radiation detector being positioned so that radiation that has passed through a subject is made incident from the substrate side.

According to the first aspect of the invention, in the radiation detector, the light-emitting layer that generates light due to irradiation of radiation and the substrate on which plural sensor portions configured to include an organic photoelectric conversion material that generates electric charges by receiving light, are disposed, are sequentially layered.

Additionally, the radiation detector is positioned in such a way that radiation that has passed through a subject is made incident from the substrate side.

In this way, according to the first aspect of the invention, the radiation that has passed through the subject is made incident from the substrate side of the radiographic imaging device, passes through the substrate, reaches the light-emitting layer, and causes the light-emitting layer to emit light, the sensor portions disposed on the substrate receive the light emitted by the light-emitting layer, and the light emission by the light-emitting layer occurs close to the substrate, so an image with high sharpness is obtained. Further, according to the present invention, the sensor portions are configured to include an organic photoelectric conversion material, and almost no radiation is absorbed by the sensor portions, so a drop in sensitivity may be suppressed.

In a second aspect of the invention, in the first aspect, it is preferred that the substrate be configured by any of plastic resin, an aramid, bio-nanofibers, or a flexible glass substrate.

Further, in a third aspect of the invention, in the above aspect thin-film transistors that are configured including an amorphous oxide in their active layers and that read out the electric charges generated in the sensor portions, may be formed on the substrate in correspondence to the sensor portions.

Further, in a fourth aspect of the invention, in the above aspect, the substrate may be adhered to an imaging region inside a casing, to which the radiation that has passed through the subject is irradiated.

Further, in a fifth aspect of the invention, in the above aspect, the light-emitting layer may be configured to include CsI columnar crystals, and the organic photoelectric conversion material may be quinacridone.

Further, in a sixth aspect of the invention, in the above aspect, the radiographic imaging device may further include: a bag body, disposed so as to overlap with a detection region in which the plural sensor portions of the radiation detector are disposed, in which at least an opposing surface opposing the detection region has an optical transparency; a tank that stores a liquid scintillator that emits light when radiation is irradiated; and an actuator that performs injection of the liquid scintillator stored in the tank into the bag body and extraction of the liquid scintillator injected into the bag body.

Further, in a seventh aspect of the invention, in the above aspect, two of the radiation detectors in which the light emission characteristics of the light-emitting layers with respect to radiation differ may be positioned to overlap each other.

Further, in an eighth aspect of the invention, in the seventh aspect, at least one change to any of the thickness of the light-emitting layers, the particle diameter of particles that fill the light-emitting layers and emit light due to irradiation of radiation, the multilayer structure of the particles, the fill rate of the particles, the doping amount of an activator, the material of the light-emitting layers, and the layer structure of the light-emitting layers, or the formation of a reflective layer that reflects the light on the sides of the light-emitting layers not opposing the substrates may be performed on the light-emitting layers of the two radiation detectors.

Moreover, in a ninth aspect of the invention, in the first and second aspects, thin-film the substrate may be further formed with transistors that read out the electric charges generated in the sensor portions, the sensor portions may be configured using a wide gap semiconductor substrate, and the light-emitting layer, the sensor portions, the thin-film transistors may be layered in this order in the radiation detector, and the radiation detector may be positioned so that the radiation is irradiated from the thin-film transistor side.

Advantageous Effects of Invention

The radiographic imaging device of the present invention may image radiographic images with high sharpness while suppressing a drop in sensitivity.

BEST MODES FOR CARRYING OUT THE INVENTION

Aspects for carrying out the present invention will be described below with reference to the drawings.

First Exemplary Embodiment

First, the configuration of an indirect conversion radiation detector 20 according to the present exemplary embodiment will be initially described.

Figure 1:
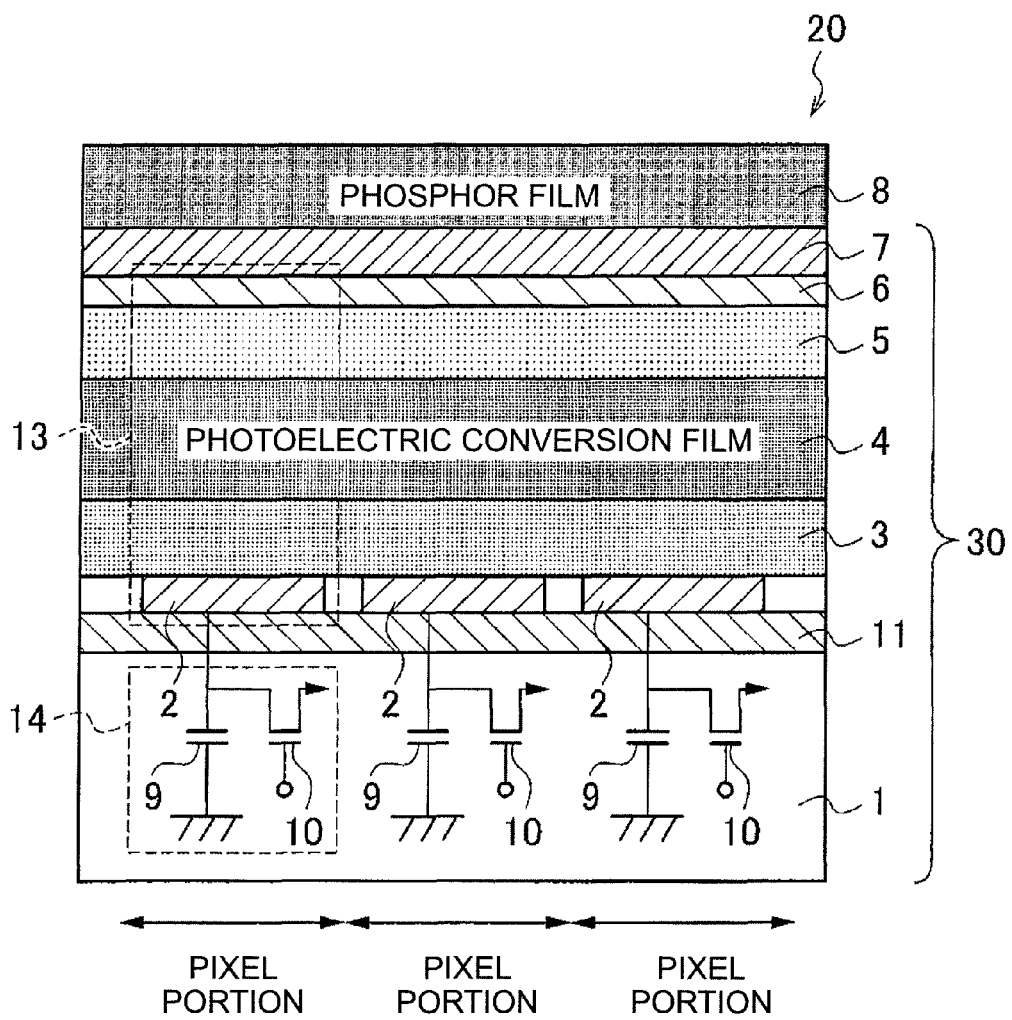
FIG. 1 is a cross-sectional schematic view showing the schematic configuration of three pixel portions of a radiation detector according to exemplary embodiments.

FIG. 1 is a cross-sectional schematic view schematically showing the configuration of three pixel portions of the radiation detector 20 which is an exemplary embodiment of the present invention.

In the radiation detector 20, signal output sections 14, sensor portions 13, and a scintillator 8 are sequentially layered on an insulating substrate 1, and pixel portions are configured by the signal output sections 14 and the sensor portions 13. The pixel portions are plurally arrayed on the substrate 1 and are configured in such a way that the signal output section 14 and the sensor portion 13 in each pixel portion overlaps.

The scintillator 8 is formed via a transparent insulating film 7 on the sensor portions 13 and is a phosphor film that converts radiation irradiated thereon from above (the opposite side of the substrate 1) into light, and emits light. The scintillator 8 absorbs the radiation that has passed through a subject and emits light.

It is preferred that the wavelength region of the light emitted by the scintillator 8 be in the visible light region (a wavelength of 360 nm to 830 nm), and it is more preferred to include the green wavelength region to enable monochrome imaging by the radiation detector 20.

As the phosphor used in the scintillator 8, specifically a phosphor including cesium iodide (CsI) is preferred in the case of performing imaging using X-rays as the radiation, and using CsI(Tl) whose emission spectrum when X-rays are irradiated is 420 nm to 700 nm, for example, is particularly preferred. The emission peak wavelength of CsI(Tl) in the visible light range is 565 nm.

The sensor portions 13 have an upper electrode 6, lower electrodes 2, and a photoelectric conversion film 4 that is positioned between the upper and lower electrodes, and the photoelectric conversion film 4 is configured by an organic photoelectric conversion material that absorbs the light emitted by the scintillator 8 and generates electric charges.

It is preferred that the upper electrode 6 be configured by a conducting material that is transparent at least with respect to the emission wavelength of the scintillator 8, because it is necessary that the upper electrode 6 allow the light generated by the scintillator 8 to be made incident on the photoelectric conversion film 4. Specifically, using a transparent conducting oxide (TCO) whose transmittance with respect to visible light is high, and whose resistance value is small, for the upper electrode 6, is preferred. A metal thin film of Au or the like may also be used as the upper electrode 6, but its resistance value tends to increase when trying to obtain a transmittance of 90% or more, so a TCO is more preferred. For example, ITO, IZO, AZO, FTO, $SnO_2$, $TiO_2$, $ZnO_2$, etc. may be preferably used, and ITO is most preferred from the standpoints of process ease, low resistance, and transparency. Note that the upper electrode 6 may have a single configuration shared by all the pixel portions or may be divided per pixel portion.

The photoelectric conversion film 4 includes the organic photoelectric conversion material, absorbs the light emitted from the scintillator 8, and generates electric charges corresponding to the absorbed light. In this way, the photoelectric conversion film 4 including the organic photoelectric conversion material has a sharp absorption spectrum in the visible region, absorbs virtually no electromagnetic waves other than the light emitted by the scintillator 8, and may effectively suppress noise generated as a result of radiation such as X-rays being absorbed by the photoelectric conversion film 4.

It is preferred that the absorption peak wavelength of the organic photoelectric conversion material, configuring the photoelectric conversion film 4, be as close as possible to the emission peak wavelength of the scintillator 8, so that the organic photoelectric conversion material most efficiently absorbs the light emitted by the scintillator 8. It is ideal that the absorption peak wavelength of the organic photoelectric conversion material and the emission peak wavelength of the scintillator 8 to be the same, but as long as the difference between them is small, the organic photoelectric conversion material may sufficiently absorb the light emitted from the scintillator 8. Specifically, it is preferred that the difference between the absorption peak wavelength of the organic photoelectric conversion material and the emission peak wavelength of the scintillator 8 with respect to radiation be within 10 nm, and it is more preferred that the difference be within 5 nm.

Examples of organic photoelectric conversion materials, that may satisfy this condition, include quinacridone organic compounds and phthalocyanine organic compounds. For example, the absorption peak wavelength of quinacridone in the visible region is 560 nm, so if quinacridone is used as the organic photoelectric conversion material and CsI(Tl) is used as the material of the scintillator 8, it becomes possible to keep the difference between the peak wavelengths within 5 nm and the amount of electric charges generated in the photoelectric conversion film 4 may be substantially maximized.

Next, the photoelectric conversion film 4 that may be applied to the radiation detector 20 according to the present exemplary embodiment will be specifically described.

The electromagnetic wave absorption/photoelectric conversion site in the radiation detector 20 according to the present invention may be configured by the pair of electrodes 2 and 6 and an organic layer including the organic photoelectric conversion film 4 sandwiched between the electrodes 2 and 6. More specifically, the organic layer may be formed by layering or mixing together a site that absorbs electromagnetic waves, a photoelectric conversion site, an electron-transporting site, a hole-transporting site, an electron-blocking site, a hole-blocking site, a crystallization preventing site, electrodes, an interlayer contact improving site, etc.

It is preferred that the organic layer include an organic p-type compound or an organic n-type compound.

Organic p-type semiconductors (compounds) are donor organic semiconductors (compounds) represented mainly by hole-transporting organic compounds and are organic compounds having the property that they easily donate electrons. More specifically, organic p-type semiconductors (compounds) are organic compounds whose ionization potential is the smaller of the two when two organic materials are brought into contact with each other and used. Consequently, any organic compound may be used as the donor organic compound provided that it is an electron-donating organic compound.

Organic n-type semiconductors (compounds) are accepter organic semiconductors (compounds) represented mainly by electron-transporting organic compounds and are organic compounds having the property that they easily accept electrons. More specifically, organic n-type semiconductors (compounds) are organic compounds whose electron affinity is the greater of the two when two organic compounds are brought into contact with each other and used. Consequently, any organic compound may be used as the accepter organic compound provided that it is an electron-accepting organic compound.

Materials that may be applied as the organic p-type semiconductor and the organic n-type semiconductor, and the configuration of the photoelectric conversion film 4, are described in detail in JP-A No. 2009-32854, so description thereof will be omitted.

As for the thickness of the photoelectric conversion film 4, it is preferred that the film thickness be as large as possible for absorbing the light from the scintillator 8. However, if the photoelectric conversion film 4 becomes thicker above a certain extent, the strength of the electric field generated in the photoelectric conversion film 4 by a bias voltage applied from both ends of the photoelectric conversion film 4 drops, and the electric charges becomes unable to be collected. For this reason, the thickness of the photoelectric conversion film 4 is preferably 30 nm to 300 nm, more preferably 50 nm to 250 nm, and particularly preferably 80 nm to 200 nm.

In the radiation detector 20 shown in FIG. 1, the photoelectric conversion film 4 has a single configuration shared by all the pixel portions, but it may also be divided per pixel portion.

The lower electrodes 2 are a thin film that has been divided per pixel portion. The lower electrodes 2 may be configured by a transparent or opaque conducting material, and aluminum, silver, etc. may be suitably used.

The thickness of the lower electrodes 2 may be 30 nm to 300 nm, for example.

In the sensor portions 13, one from among the electric charges (holes and electrons) generated in the photoelectric conversion film 4, may be moved to the upper electrode 6 and the other may be moved to the lower electrodes 2, by applying a predetermined bias voltage between the upper electrode 6 and the lower electrodes 2. In the radiation detector 20 of the present embodiment, a wire is connected to the upper electrode 6, and the bias voltage is applied to the upper electrode 6 via this wire. Further, the polarity of the bias voltage is decided so that the electrons generated in the photoelectric conversion film 4 move to the upper electrode 6 and the holes move to the lower electrodes 2, but this polarity may also be the opposite.

The sensor portions 13 configuring each of the pixel portions may include at least the lower electrodes 2, the photoelectric conversion film 4, and the upper electrode 6. However, to suppress an increase in dark current, disposing at least either of an electron-blocking film 3 and a hole-blocking film 5 in the sensor portions 13 is preferred, and disposing both is more preferred.

The electron-blocking film 3 may be disposed between the lower electrodes 2 and the photoelectric conversion film 4 and may suppress electrons from being injected from the lower electrodes 2 into the photoelectric conversion film 4 and dark current from increasing, when the bias voltage has been applied between the lower electrodes 2 and the upper electrode 6.

Electron-donating organic materials may be used for the electron-blocking film 3.

The material that is actually used for the electron-blocking film 3 may be selected in accordance with, for example, the material of the adjacent electrodes and the material of the adjacent photoelectric conversion film 4; a material whose electron affinity (Ea) is greater by 1.3 eV or more than the work function (Wf) of the material of the adjacent electrodes and has an ionization potential (Ip) equal to or smaller than the ionization potential of the material of the adjacent photoelectric conversion film 4, is preferred. Materials that may be applied as the electron-donating organic material are described in detail in JP-A No. 2009-32854, so description thereof will be omitted. The photoelectric conversion film 4 may also be formed to further include fullerenes or carbon nanotubes.

In order to allow the electron-blocking film 3 to reliably exhibit a dark current suppressing effect and to prevent a drop in the photoelectric conversion efficiency of the sensor portions 13, the thickness of the electron-blocking film 3 is preferably 10 nm to 200 nm, more preferably 30 nm to 150 nm, and particularly preferably 50 nm to 100 nm.

The hole-blocking film 5 may be disposed between the photoelectric conversion film 4 and the upper electrode 6, and may suppress holes from being injected from the upper electrode 6 into the photoelectric conversion film 4 and dark current from increasing when the bias voltage has been applied between the lower electrodes 2 and the upper electrode 6.

Electron-accepting organic materials may be used for the hole-blocking film 5.

In order to allow the hole-blocking film 5 to reliably exhibit a dark current suppressing effect and to prevent a drop in the photoelectric conversion efficiency of the sensor portions 13, the thickness of the hole-blocking film 5 is preferably 10 nm to 200 nm, more preferably 30 nm to 150 nm, and particularly preferably 50 nm to 100 nm.

The material that is actually used for the hole-blocking film 5 may be selected in accordance with, for example, the material of the adjacent electrode and the material of the adjacent photoelectric conversion film 4; a material whose ionization potential (Ip) is greater by 1.3 eV or more than the work function (Wf) of the material of the adjacent electrode and has an electron affinity (Ea) equal to or greater than the electron affinity of the material of the adjacent photoelectric conversion film 4, is preferred. Materials that may be applied as the electron-accepting organic material are described in detail in JP-A No. 2009-32854, so description thereof will be omitted.

In the case of setting the bias voltage in such a way that, from among the electric charges generated in the photoelectric conversion film 4, the holes move to the upper electrode 6 and the electrons move to the lower electrode 2, it suffices to reverse the positions of the electron-blocking film 3 and the hole-blocking film 5. Further, the electron-blocking film 3 and the hole-blocking film 5 do not both have to be disposed; a certain degree of a dark current suppressing effect may be obtained as long as either is disposed.

The signal output sections 14 are formed on the front side of the substrate 1 below the lower electrodes 2 of each of the pixel portions.

Figure 2:
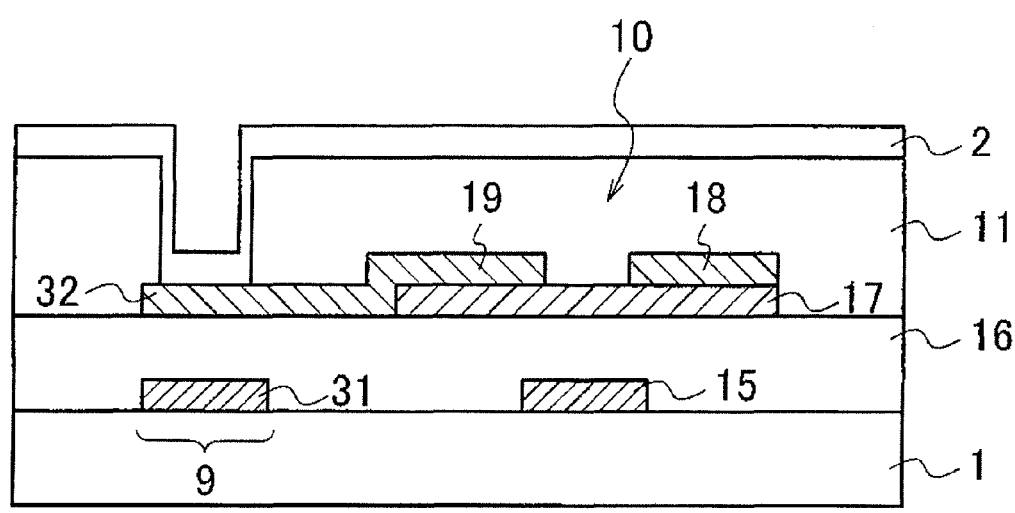
FIG. 2 is a cross-sectional view schematically showing the configuration of a signal output section of one pixel portion of the radiation detector according to the exemplary embodiments.

In FIG. 2, the configuration of the signal output sections 14 is schematically shown.

A capacitor 9 that stores the electric charges that has moved to the lower electrode 2 and a field-effect thin-film transistor (TFT; hereinafter there are cases where this is simply called a "thin-film transistor") 10 that converts the electric charges stored in the capacitor 9 into an electrical signal, and outputs the electrical signal are formed in correspondence to the lower electrode 2. The region in which the capacitor 9 and the thin-film transistor 10 are formed has a section that overlaps with the lower electrode 2 as seen in a plan view. By giving the signal output section 14 this configuration, the signal output section 14 and the sensor portion 13 in each of the pixel portions lie on top of each another in the thickness direction. To minimize the plane area of the radiation detector 20 (the pixel portions), it is preferred that the region in which the capacitor 9 and the thin-film transistor 10 are formed be completely covered by the lower electrode 2.

The capacitor 9 is electrically connected to the corresponding lower electrode 2 via a wire of a conducting material that is formed penetrating an insulating film 11 disposed between the substrate 1 and the lower electrode 2. Because of this, the electric charges trapped in the lower electrode 2 may be moved to the capacitor 9.

In the thin-film transistor 10, a gate electrode 15, a gate insulating film 16, and an active layer (channel layer) 17 are layered, and moreover, a source electrode 18 and a drain electrode 19 are formed a predetermined spacing apart from each other on the active layer 17.

The active layer 17 may be formed by amorphous silicon, an amorphous oxide, an organic semiconductor material, or carbon nanotubes, for example. The material configuring the active layer 17 is not limited to these.

As the amorphous oxide that may configure the active layer 17, an oxide including at least one of In, Ga, and Zn (e.g., In—O) is preferred, an oxide including at least two of In, Ga, and Zn (e.g., In—Zn—O, In—Ga—O, and Ga—Zn—O) is more preferred, and an oxide including In, Ga, and Zn is particularly preferred. As an In—Ga—Zn—O amorphous oxide, an amorphous oxide whose composition in a crystalline state is expressed by $InGaO_3(ZnO)_m$ (where m is a natural number less than 6) is preferred, and particularly $InGaZnO_4$ is more preferred. The amorphous oxide that may configure the active layer 17 is not limited to these.

Examples of organic semiconductor materials that may configure the active layer 17 include phthalocyanine compounds, pentacene, and vanadyl phthalocyanine but are not limited to these. Configurations of phthalocyanine compounds are described in detail in JP-A No. 2009-212389, so description thereof will be omitted.

By forming the active layer 17 of the thin-film transistor 10 using an amorphous oxide, an organic semiconductor material, or carbon nanotubes, the active layer 17 does not absorb radiation such as X-rays, or if it does absorb any radiation the amount absorbed is only an extremely minute amount, so the generation of noise in the signal output section 14 may be effectively suppressed.

Further, in a case where the active layer 17 is formed using carbon nanotubes, the switching speed of the thin-film transistor 10 may be increased, and the thin-film transistor 10 may be formed having a low degree of absorption of light in the visible light range. In the case of forming the active layer 17 using carbon nanotubes, the performance of the thin-film transistor 10 drops significantly when an infinitesimal amount of a metal impurity is mixed into the active layer 17, so it is necessary to separate, extract, and form extremely high-purity carbon nanotubes by centrifugal separation or the like.

Here, the amorphous oxide, organic semiconductor material, carbon nanotubes, and organic photoelectric conversion material may all be formed into films at a low temperature. Consequently, the substrate 1 is not limited to a substrate with high heat resistance, such as a semiconductor substrate, a quartz substrate, and a glass substrate, and a flexible substrate of plastic or the like, an aramid, or bio-nanofibers may also be used. Specifically, polyester, such as polyethylene terephthalate, polybutylene phthalate, and polyethylene naphthalate, polystyrene, polycarbonate, polyethersulphone, polyarylate, polyimide, polycyclic olefin, norbornene resin, and poly(chloro-trifluoro-ethylene) or other flexible substrates may be used. By using a flexible substrate made of plastic, the substrate may be made lightweight, which becomes advantageous for portability, for example.

Further, an insulating layer for ensuring insulation, a gas barrier layer for preventing the transmission of moisture and oxygen, an undercoat layer for improving flatness or adhesion to the electrodes or the like, and other layers, may also be disposed on the substrate 1.

Aramids may be applied to high-temperature processes reaching 200 degrees or higher, so a transparent electrode material may be hardened at a high temperature and given a low resistance, and aramids may also handle automatic packaging of driver ICs including solder reflow processes. Further, aramids have a thermal expansion coefficient that is close to that of indium tin oxide (ITO) or a glass substrate, so they have little warping after manufacture and do not break easily. Further, aramids may also form a thinner substrate compared to a glass substrate or the like. An ultrathin glass substrate and an aramid may also be layered to form the substrate 1.

Bio-nanofibers are composites of cellulose microfibril bundles (bacterial cellulose) that a bacterium (*Acetobacter xylinum*) produces and a transparent resin. Cellulose microfibril bundles have a width of 50 nm, which is a size that is 1/10 with respect to visible wavelengths, and have high strength, high elasticity, and low thermal expansion. By impregnating and hardening a transparent resin such as an acrylic resin or an epoxy resin in bacterial cellulose, bio-nanofibers exhibiting a light transmittance of about 90% at a wavelength of 500 nm while including fibers at 60 to 70% may be obtained. Bio-nanofibers have a low thermal expansion coefficient (3 to 7 ppm) comparable to silicon crystal, a strength comparable to steel (460 MPa), high elasticity (30 GPa), and are flexible, so they may form a thinner substrate 1 compared to a glass substrate or the like.

In the present exemplary embodiment, the radiation detector 20 is formed by forming the signal output sections 14, the sensor portions 13, and the transparent insulating film 7 in order on the substrate 1 and adhering the scintillator 8 on the substrate 1 using an adhesive resin or the like whose light absorbance is low. Below, the substrate 1 formed up to the transparent insulating film 7 will be called a TFT substrate 30.

Figure 3:
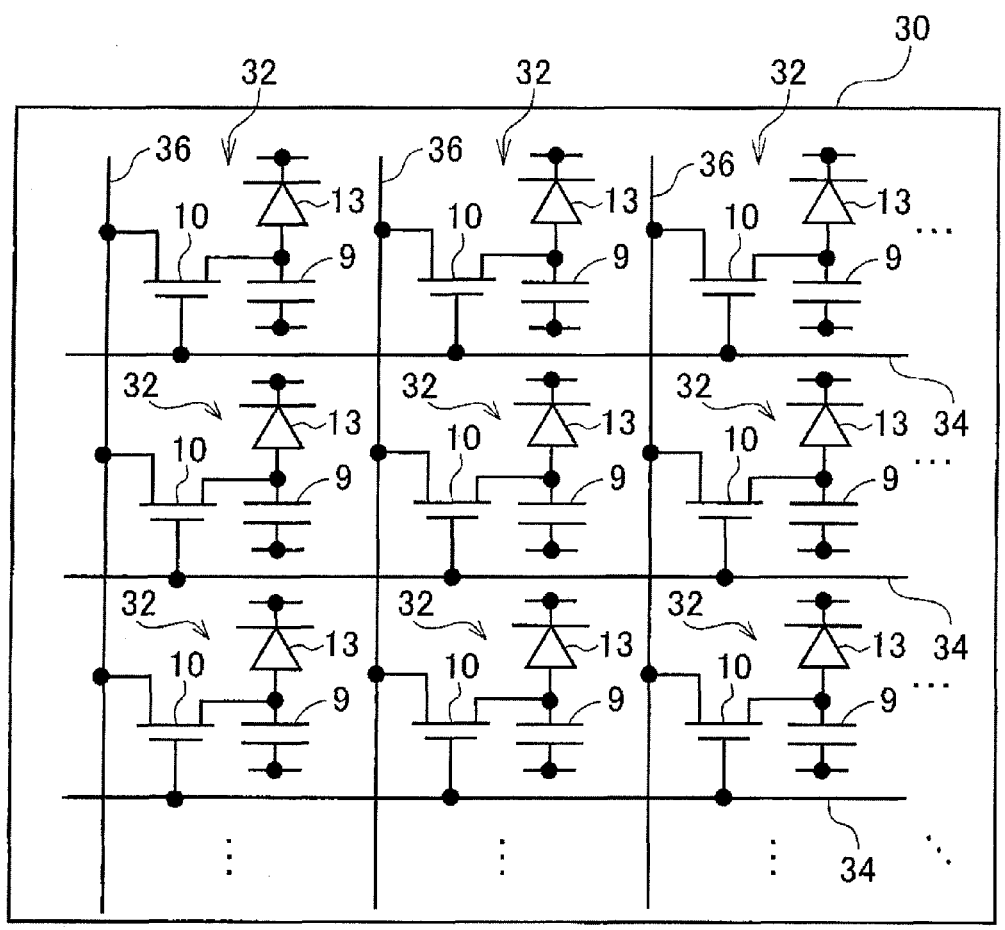
FIG. 3 is a plan view showing the configuration of the radiation detector according to the exemplary embodiments.

As shown in FIG. 3, on the TFT substrate 30, pixels 32 configured to include the sensor portions 13, the capacitors 9, and the thin-film transistors 10 are plurally disposed two-dimensionally in one direction (a row direction in FIG. 3) and an intersecting direction (a column direction in FIG. 3) with respect to the one direction.

Further, plural gate lines 34, which are disposed extending in the one direction (the row direction) and are for switching ON and OFF the thin-film transistors 10, and plural data lines 36, which are disposed extending in the intersecting direction (the column direction) and are for reading out the electric charges via the thin-film transistors 10 in an on-state, are disposed in the radiation detector 20.

The radiation detector 20 is shaped like a flat plate and has a four-sided shape having four sides on its outer edge as seen in a plan view. Specifically, it is formed in the shape of a rectangle.

Next, the configuration of a portable radiographic imaging device (called an "electronic cassette" below) 40 that has the radiation detector 20 therein and that images radiographic images, will be described.

Figure 4:
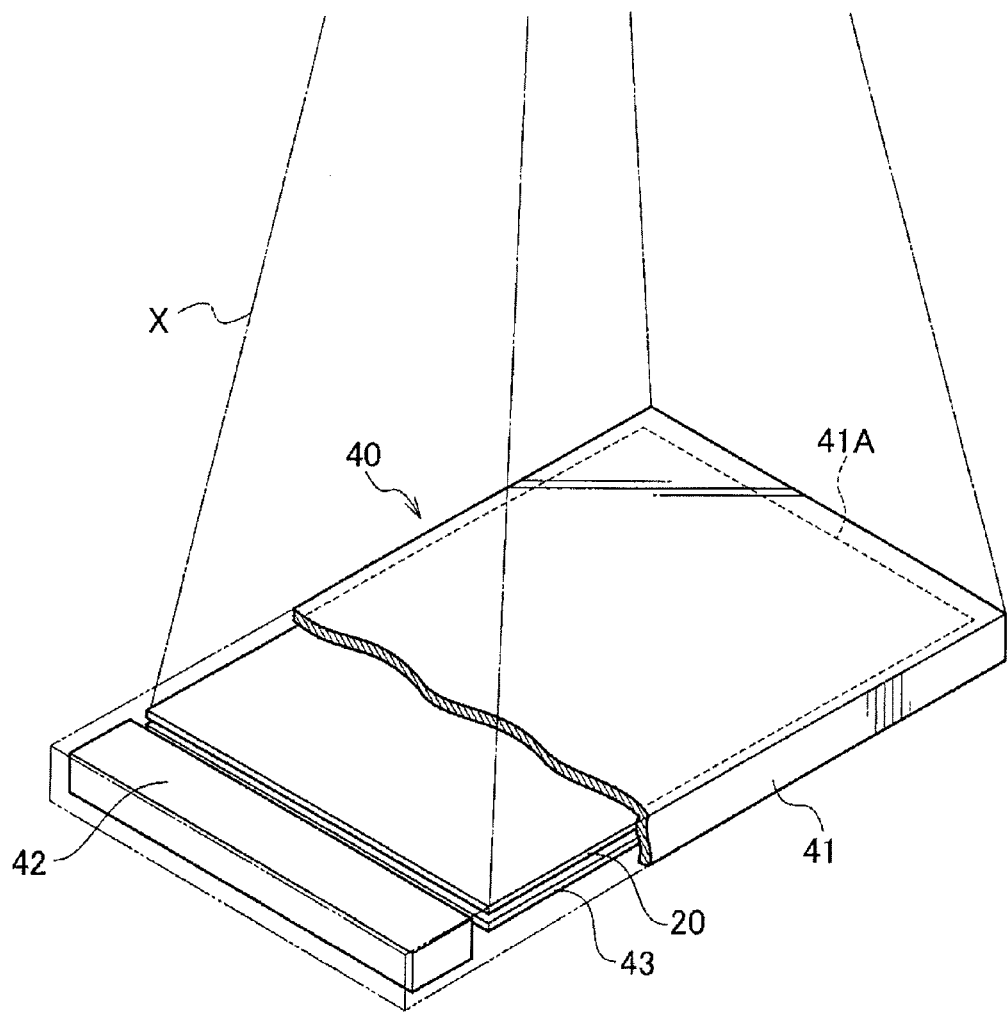
FIG. 4 is a perspective view showing the configuration of an electronic cassette according to a first exemplary embodiment.

In FIG. 4, there is shown a perspective view showing the configuration of the electronic cassette 40.

Figure 5:
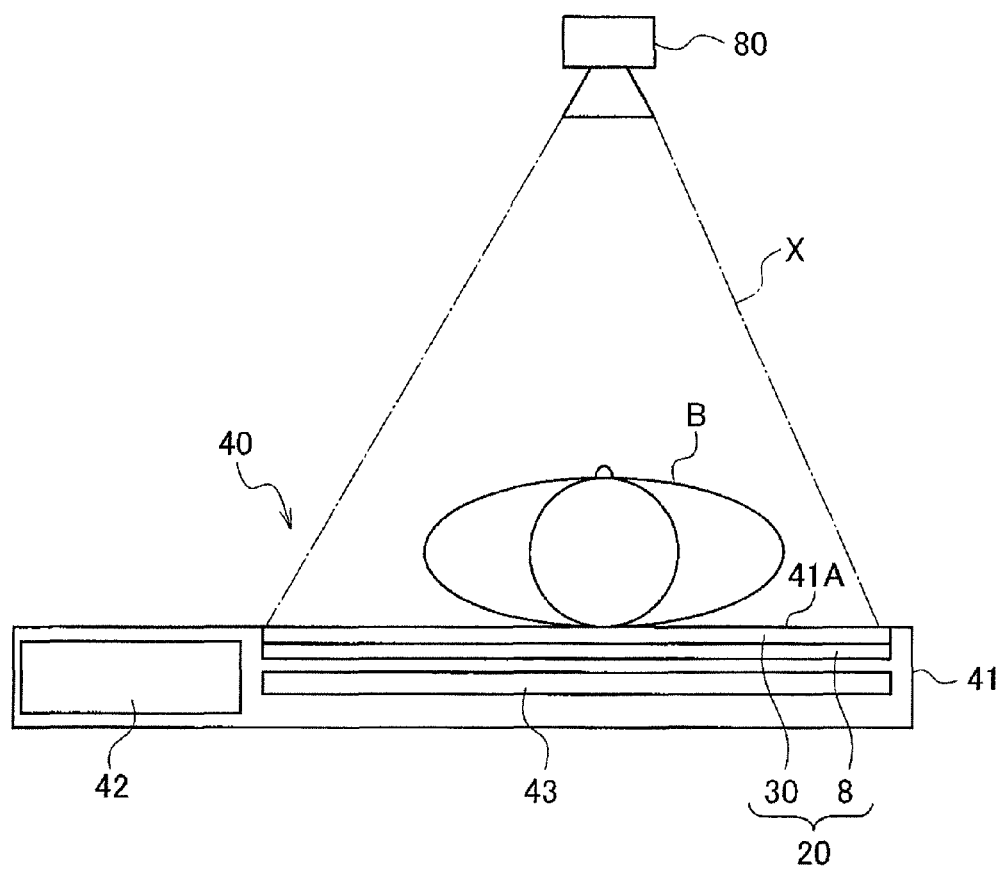
FIG. 5 is a cross-sectional view showing the configuration of the electronic cassette according to the first exemplary embodiment.

The electronic cassette 40 is equipped with a flat plate-shaped casing 41 including a material that allows radiation to pass through, and the electronic cassette 40 is given a waterproof and airtight structure. The radiation detector 20, which detects radiation X that has passed through the subject from irradiated side of the casing 51 to which the radiation X is irradiated, and a lead plate 43, which absorbs backscatter rays of the radiation X, are disposed in order inside the casing 41. A region of the casing 41 corresponding to the disposed position of the radiation detector 20 in one surface of the flat plate shape serves as an imaging region 41A with a four-sided shape that may detect the radiation. As shown in FIG. 5, the radiation detector 20 is positioned so that the TFT substrate 30 is on the imaging region 41A side, and the radiation detector 20 is adhered to the inside of the casing 41 configuring the imaging region 41A.

Further, a case 42 that accommodates a cassette control section 58 and a power source section 70, described later, is positioned on one end side of the inside of the casing 41 in a position that does not overlap with the radiation detector 20 (outside the range of the imaging region 41A).

Figure 6:
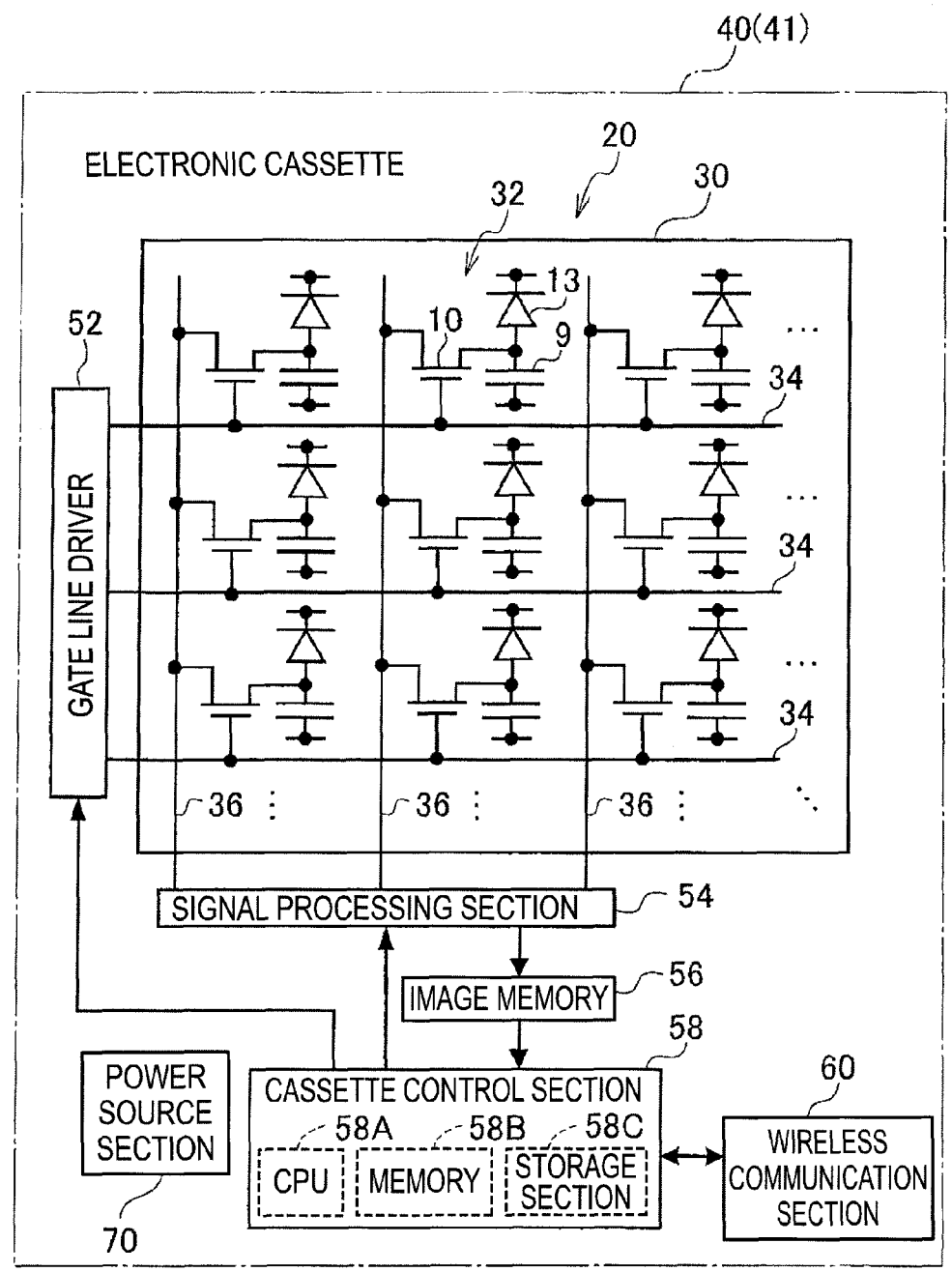
FIG. 6 is a block diagram showing the configurations of main sections of an electrical system of the electronic cassette according to the first exemplary embodiment.

In FIG. 6, there is shown a block diagram showing the configurations of main sections of an electrical system of the electronic cassette 40 according to the present exemplary embodiment.

In the radiation detector 20, a gate line driver 52 is positioned on one side of two sides adjacent to each other, and a signal processing section 54 is positioned on the other side. The individual gate lines 34 of the TFT substrate 30 are connected to the gate line driver 52, and the individual data lines 36 of the TFT substrate 30 are connected to the signal processing section 54.

Further, an image memory 56, a cassette control section 58, and a wireless communication section 60 are disposed inside the casing 41.

The thin-film transistors 10 of the TFT substrate 30 are sequentially switched ON in row units, by signals supplied via the gate lines 34 from the gate line driver 52, and the electric charges that have been read out by the thin-film transistors 10 switched to ON-state are transmitted through the data lines 36 as electrical signals and are input to the signal processing section 54. Because of this, the electric charges are sequentially read out in row units, and two-dimensional radiographic images become acquirable.

Although not shown in the drawings, the signal processing section 54 has, for each of the individual data lines 36, amplification circuits that amplify the input electrical signals and sample-and-hold circuits, and the electrical signals that have been transmitted through the individual data lines 36 are amplified by the amplification circuits and are thereafter held in the sample-and-hold circuits. Further, multiplexers and analog-to-digital (A/D) converters are connected in order to the output sides of the sample-and-hold circuits, and the electrical signals held in the individual sample-and-hold circuits are sequentially input (serially) to the multiplexers, and are converted into digital image data by the A/D converters.

The image memory 56 is connected to the signal processing section 54, and the image data that have been output from the A/D converters of the signal processing section 54 are sequentially stored in the image memory 56. The image memory 56 has a storage capacity that may store a predetermined number of frames' worth of image data, and each time radiographic imaging is performed, the image data obtained by the imaging are sequentially stored in the image memory 56.

The image memory 56 is also connected to the cassette control section 58. The cassette control section 58 is configured by a microcomputer, is equipped with a central processing unit (CPU) 58A, a memory 58B including a ROM and a RAM, and a non-volatile storage section 58C comprising a flash memory or the like, and controls the operations of the entire electronic cassette 40.

Further, the wireless communication section 60 is connected to the cassette control section 58. The wireless communication section 60 is compatible with a wireless local area network (LAN) standard represented by the Institute of Electrical and Electronics Engineers (IEEE) 802.11a/b/g/n standard or the like, and controls the transmission of various types of information between the electronic cassette 40 and external devices by wireless communication. The cassette control section 58 may wirelessly communicate with external devices, such as a console that controls radiographic imaging overall, via the wireless communication section 60 and may transmit and receive various types of information to and from the console via the wireless communication section 60.

Further, a power source section 70 is disposed in the electronic cassette 40, and the various circuits and elements described above (the gate line driver 52, the signal processing section 54, the image memory 56, the wireless communication section 60, the microcomputer functioning as the cassette control section 58, etc.) operate on power supplied from the power source section 70. The power source section 70 has a built in battery (a rechargeable secondary battery) so as to not impair the portability of the electronic cassette 40, and the power source section 70 supplies power to the various circuits and elements from the charged battery. Note that, in FIG. 6, illustration of wires connecting the various circuits and elements to the power source section 70 is omitted.

Next, the operations of the electronic cassette 40 according to the present exemplary embodiment will be described.

When imaging a radiographic image, the electronic cassette 40 according to the present exemplary embodiment is positioned with the imaging region 41A face-up, and, as shown in FIG. 5, the electronic cassette 40 is spaced apart from a radiation generator 80 that generates radiation, and an imaging target site B of the patient is positioned above the imaging region. The radiation generator 80 emits a dose of radiation X corresponding to imaging conditions and so forth, that have been given beforehand. The radiation X emitted from the radiation generator 80 carries image information as a result of passing through the imaging target site B and is thereafter irradiated to the electronic cassette 40.

The radiation X irradiated from the radiation generator 80 passes through the imaging target site B and thereafter reaches the electronic cassette 40. Because of this, electric charges corresponding to the dose of radiation X that has been irradiated are generated in the sensor portions 13 of the radiation detector 20 built in the electronic cassette 40, and the electric charges generated in the sensor portions 13 are stored in the capacitors 9.

After the application of the radiation X ends, the cassette control section 58 controls the gate line driver 52 to cause ON signals to be sequentially output, one line at a time, from the gate line driver 52 to the gate lines 34 of the radiation detector 20 to thereby read out the image information. The image information read out from the radiation detector 20 is stored in the image memory 56.

Incidentally, as shown in FIG. 5, in the electronic cassette 40 according to the present exemplary embodiment, the radiation detector 20 is built therein so that the radiation X is irradiated from the TFT substrate 30 side.

Figure 7:
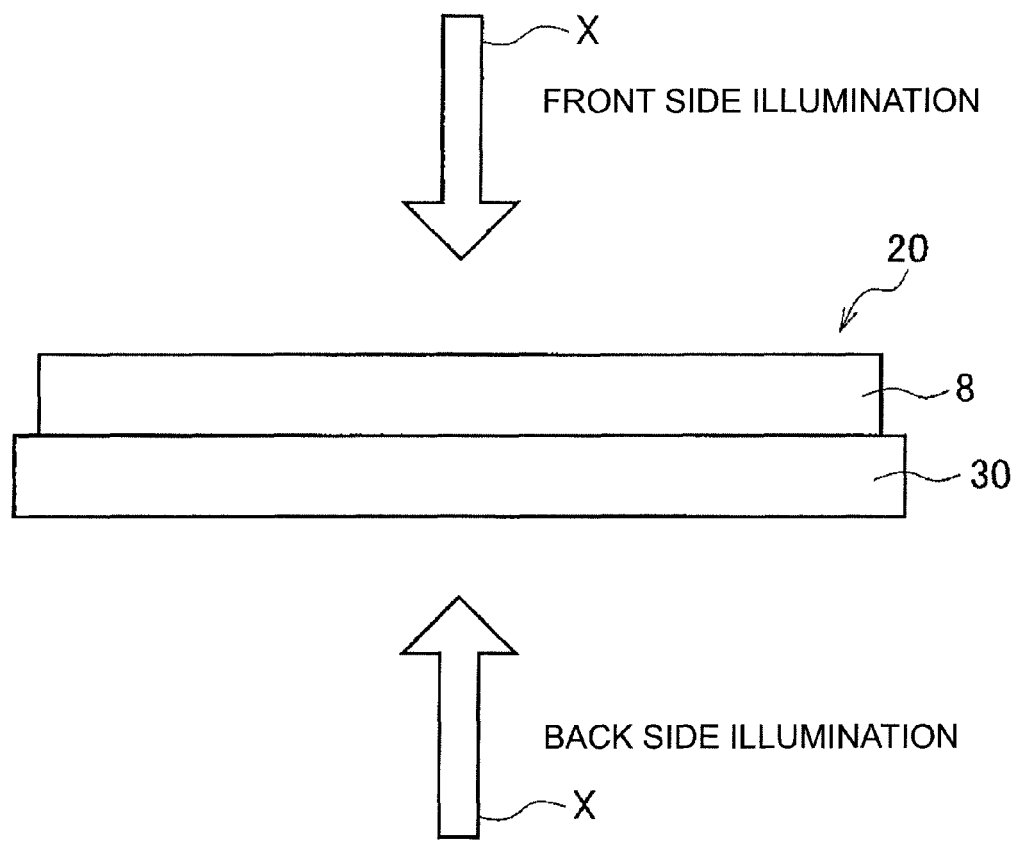
FIG. 7 is a cross-sectional view for describing front side irradiation and back side irradiation of the radiation detector with radiation X.

Here, as shown in FIG. 7, in a case where the radiation X is irradiated to the radiation detector 20 from the front side on which the scintillator 8 is formed (also called "front side irradiation" and "rear side reading" (so-called penetration side sampling, or PSS)), light is emitted more strongly on the upper side of the scintillator 8 (the opposite side of the TFT substrate 30), and in a case where the radiation X is irradiated to the radiation detector 20 from the TFT substrate 30 side (back side) (also called "back side irradiation" or "front side reading" (so-called irradiation side sampling, or ISS)), the radiation X that has passed through the TFT substrate 30 is made incident on the scintillator 8, and the TFT substrate 30 side of the scintillator 8 emits light more strongly. In the sensor portions 13 disposed on the TFT substrate 30, electric charges are generated by the light generated by the scintillator 8. For this reason, the light emission position of the scintillator 8 with respect to the TFT substrate 30 is closer in a case where the radiation X is irradiated from the back side of the radiation detector 20 than in a case where the radiation X is irradiated from the front side of the radiation detector 20, so the resolution of the radiographic image obtained by imaging is higher.

Further, the photoelectric conversion film 4 of the radiation detector 20 is configured by an organic photoelectric conversion material, and almost no radiation is absorbed by the photoelectric conversion film 4. For this reason, in the radiation detector 20 according to the present exemplary embodiment, the amount of radiation absorbed by the photoelectric conversion film 4 is small even in a case where the radiation passes through the TFT substrate 30 because of back side irradiation, so a drop in sensitivity with respect to the radiation X may be suppressed. In back side irradiation, the radiation passes through the TFT substrate 30 and reaches the scintillator 8, but in a case where the photoelectric conversion film 4 of the TFT substrate 30 is configured by an organic photoelectric conversion material in this way, there is almost no absorption of the radiation by the photoelectric conversion film 4, and attenuation of the radiation may be kept small, and therefore is suited to back side irradiation.

Further, the amorphous oxide configuring the active layers 17 of the thin-film transistors 10 and the organic photoelectric conversion material configuring the photoelectric conversion film 4 may both be formed into films at a low temperature. For this reason, the substrate 1 may be formed by plastic resin, an aramid, or bio-nanofibers in which there is little absorption of radiation. In the substrate 1 formed in this way, the amount of radiation absorbed is small, so a drop in sensitivity with respect to the radiation X may be suppressed even in a case where the radiation passes through the TFT substrate 30 because of back side irradiation.

Further, according to the present exemplary embodiment, as shown in FIG. 5, the radiation detector 20 is adhered to the imaging region 41A section inside the casing 41 in such a way that the TFT substrate 30 is on the imaging region 41A side, but in a case where the substrate 1 is formed by plastic resin, an aramid, or bio-nanofibers whose rigidity is high, the rigidity of the radiation detector 20 itself is high, so the imaging region 41A section of the casing 41 may be formed thin. Further, in a case where the substrate 1 is formed by plastic resin, an aramid, or bio-nanofibers whose rigidity is high, the radiation detector 20 itself has flexibility, so it is difficult for the radiation detector 20 to sustain damage even in a case where shock has been imparted to the imaging region 41A.

Further, the radiation detector 20 is obtained by forming the scintillator 8 on a support body and thereafter superposing this with and placing it on the TFT substrate 30. However, the method of superposing the scintillator 8 and the TFT substrate 30 is not particularly limited, and both may be optically coupled. As the method of superposing and placing both, either a method in which both are made to oppose each other and are directly brought into close contact with each other or a method in which both are brought into close contact with each other via some kind of adhesive layer and a flattening layer may be employed.

Figure 27:
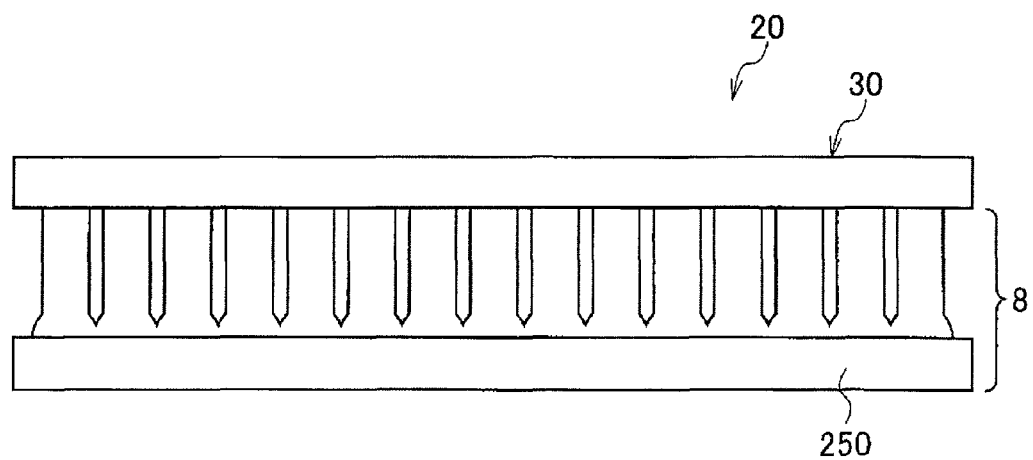
FIG. 27 is a cross-sectional view showing an example of the configuration of a radiation detector according to an exemplary embodiment.

Further, for example, as shown in FIG. 27, in a case where CsI(Tl) columnar crystals are formed by deposition on a deposition substrate 250, for example, as the scintillator 8, the photoelectric conversion film 4 of the sensor portions 13 of the TFT substrate 30 is formed by quinacridone, and the scintillator 8 and the TFT substrate 30 are adhered together in such a way that the side on which the columnar crystals have been formed faces the TFT substrate 30 to form the radiation detector 20, the modulation transfer function (MTF) characteristic of the radiographic images obtained by imaging may be improved.

Figure 28:
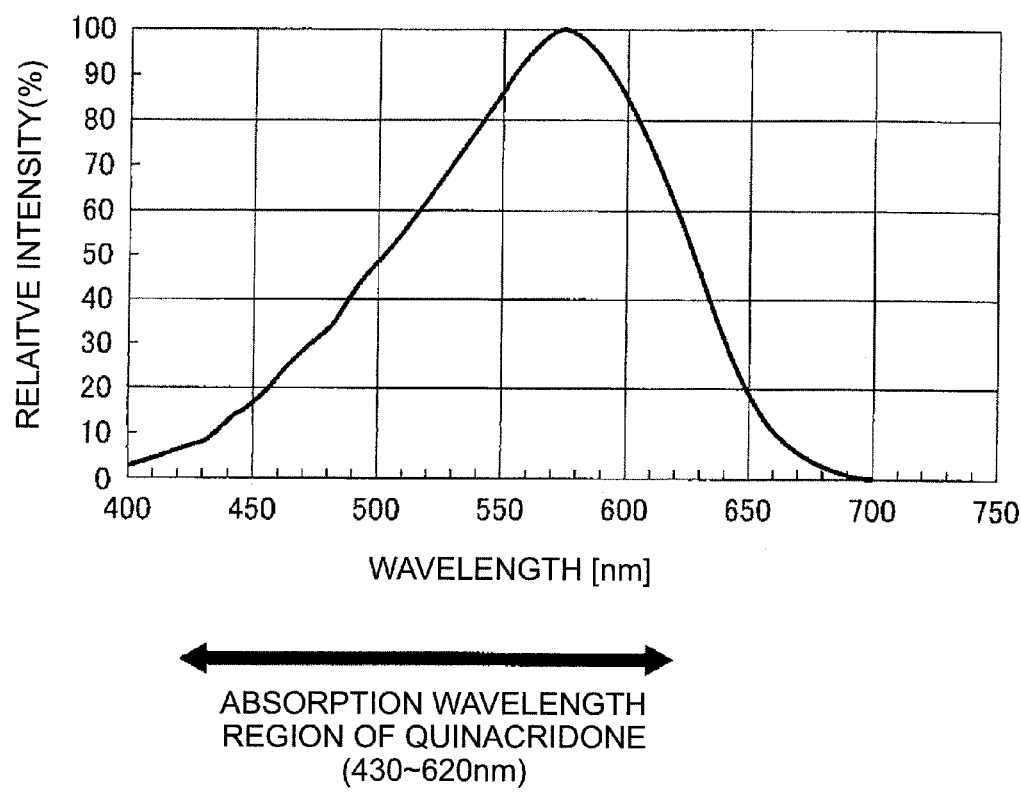
FIG. 28 is a graph showing the light emission characteristic of CsI(Tl) and the absorption wavelength range of quinacridone.

As shown in FIG. 28, CsI(Tl) has an emission peak wavelength of 565 nm, but light of a relatively wide wavelength region (400 nm to 700 nm) is included in the emitted light. On the other hand, quinacridone is sensitive to light in the wavelength region of 430 nm to 620 nm.

Figure 29:
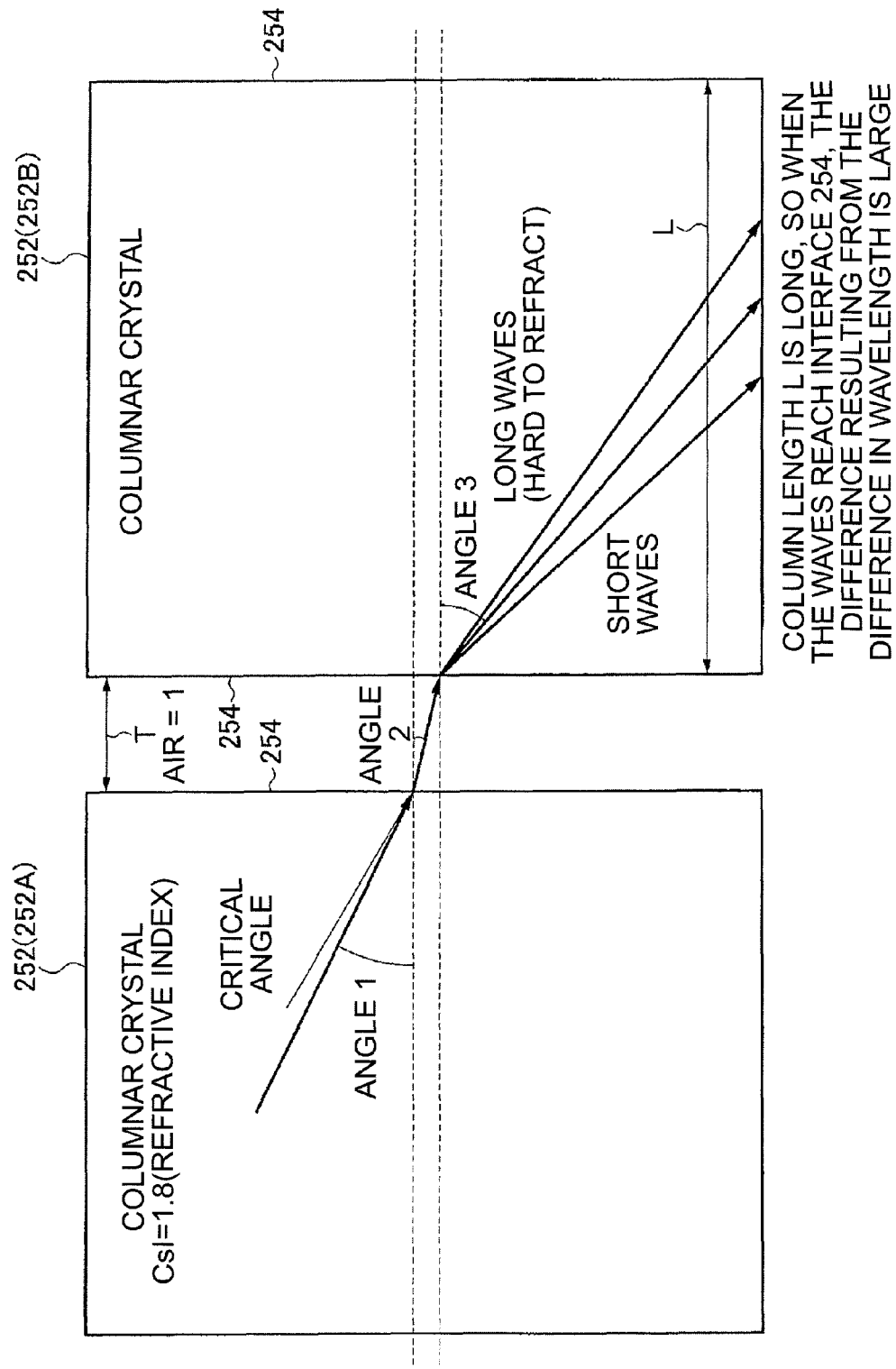
FIG. 29 is a schematic enlarged view in which columnar crystals and a sensor portion section of the radiation detector are enlarged.

Further, in a case where the scintillator 8 comprises CsI(Tl) columnar crystals, light is generated inside the columnar crystals as a result of the radiation being irradiated. As shown in FIG. 29, as for the light generated inside columnar crystals 252, in a case where the incident angle θ at which the light is made incident on interfaces 254 of the columnar crystals with the outside exceeds the critical angle (e.g., 34°) at which the light is totally reflected, the light is totally reflected inside the columnar crystals 252, and in a case where the angle of incidence is within the critical angle, some of the light passes to the outside. For this reason, as shown in FIG. 29, there are cases where the light that has passed through a columnar crystal 252A is made incident on an adjacent columnar crystal 252B. This passing light is refracted at the interfaces 254 and its traveling direction changes. Angle 1 at which the light generated in the columnar crystal 252A and passing to the outside is made incident on the interface 254, angle 2 at which the light exits the interface 254, and angle 3 at which the light that has passed to the outside exits from the interface 254 of the adjacent columnar crystal 252B has the relationship of angle 1>angle 2<angle 3. Further, the angular change in angle 3 with respect to angle 1 in the traveling direction resulting from refraction is greater the shorter the wavelength of light and is smaller the longer the wavelength of light. The longer the wavelength of the light that has passed to the columnar crystal 252B, the smaller the angular change resulting from refraction, so the probability that the light will end up passing through again without being totally reflected by the interface 254 of the columnar crystal 254B is high, and as a result, the longer the wavelength of the light, the farther the position that the light reaches, and a phenomenon in which the light is made incident on the sensor portions 13 of other pixels 32 tends to occur. FIG. 29 shows a case in which the fill rate of the columnar crystals 252 has been made high (e.g., 80%), and the interval T between the columnar crystals 252 is short, so the path of the light between the columnar crystals 252 is regarded as identical irrespective of wavelength.

However, in a case where the photoelectric conversion film 4 of the radiation detection 20 is formed by quinacridone, the sensitivity of the sensor portions 13 may be kept low with respect to long-wavelength light that tends to reach other pixels 32, so the MTF characteristic may be improved.

In particular, it is required that radiographic imaging devices for breasts (so-called mammography), which image radiographic images of the breasts of a subject, vividly image microscopic sites such as microscopic calcifications, and the pixels 32 of the radiation detector 20 are also formed in a small size and in high definition. In a case where the pixels 32 of the radiation detector 20 are formed in high definition, the distance between the pixels also becomes shorter and it becomes easier for the pixels 32 to be affected by the light from other pixels 32. For this reason, in the radiation detector 20 used in a radiographic imaging device for breasts, forming the scintillator 8 using CsI(Tl) columnar crystals and forming the photoelectric conversion film 4 of the sensor portions 13 of the TFT substrate 30 using quinacridone is effective for imaging vivid radiographic images.

Second Exemplary Embodiment

Next, a second exemplary embodiment will be described. In regard to sections that are identical to those in the first exemplary embodiment, identical reference signs will be given thereto and description thereof will be omitted, and only sections that are different will be described.

First, the configuration of an imaging section 21 that images radiographic images will be described.

The imaging section 21 according to the present exemplary embodiment has two imaging systems that image radiographic images represented by irradiated radiation and is configured so that it may individually read out sets of image information representing the radiographic images imaged by the imaging systems.

Figure 8:
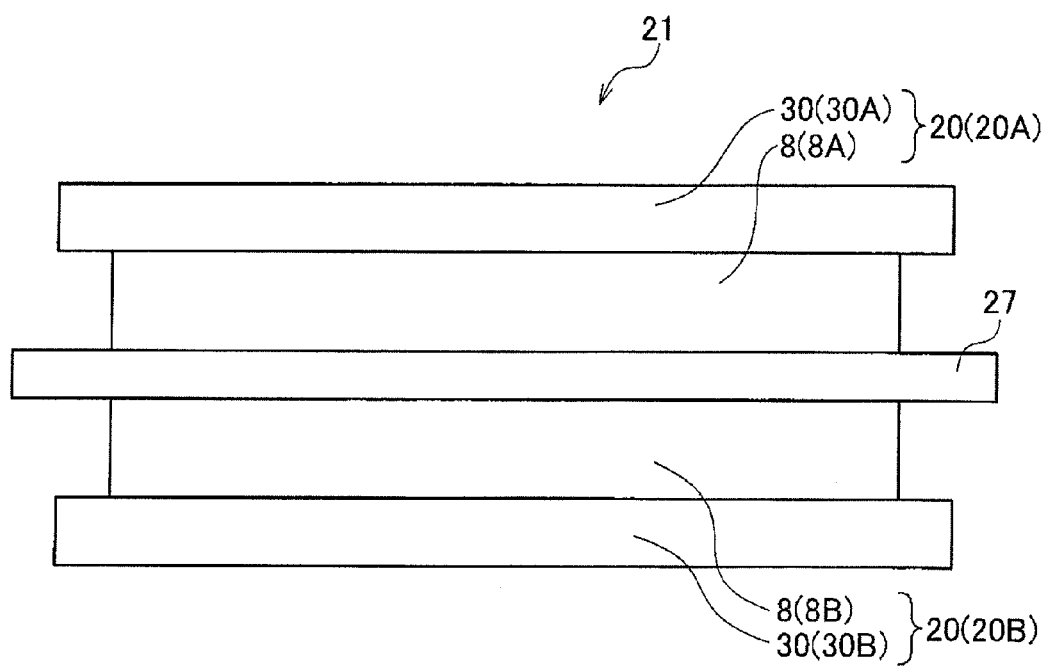
FIG. 8 is a cross-sectional view showing the configuration of an imaging section according to a second exemplary embodiment.

Namely, as shown in FIG. 8, two radiation detectors 20 (20A and 20B) are positioned so that their scintillator 8 sides oppose each other, with a light-blocking plate 27 that allows radiation to pass through and blocks light being interposed in between. Below, in the case of distinguishing between the scintillators 8 and the TFT substrates 30 of the two radiation detectors 20A and 20B, the letter A will be added to the scintillator 8 and the TFT substrate 30 of the radiation detector 20A, and the letter B will be added to the scintillator 8 and the TFT substrate 30 of the radiation detector 20B.

In this way, because the scintillator 8A and the TFT substrate 30A are disposed in order on one side of the light-blocking plate 27, in the radiation detector 20A the application of the radiation from the one side becomes back side irradiation, and because the scintillator 8B and the TFT substrate 30B are disposed in order on the other side of the light-blocking substrate 27, in the radiation detector 20B the application of the radiation from the other side becomes back side irradiation. Further, by disposing the light-blocking plate 27 between the two radiation detectors 20A and 20B, the light generated by the scintillator 8A does not pass through to the scintillator 8B side and the light generated by the scintillator 8B does not pass through to the scintillator 8A side.

Here, the light emission characteristic of the scintillator 8 changes depending also on its thickness, so the thicker the scintillator 8 becomes, the greater the light emission amount of the scintillator 8 becomes and the higher the sensitivity of the scintillator 8 becomes, but image quality deteriorates because of light scattering and so forth.

Further, in a case where the scintillator 8 is formed by filling it with particles that emit light due to irradiation of radiation, such as GOS, for example, the larger the particle diameter of the particles is, the greater the light emission amount of the scintillator 8 becomes and the higher the sensitivity of the scintillator 8 becomes, but light scattering increases and affects adjacent pixels, so image quality deteriorates.

Figure 9:
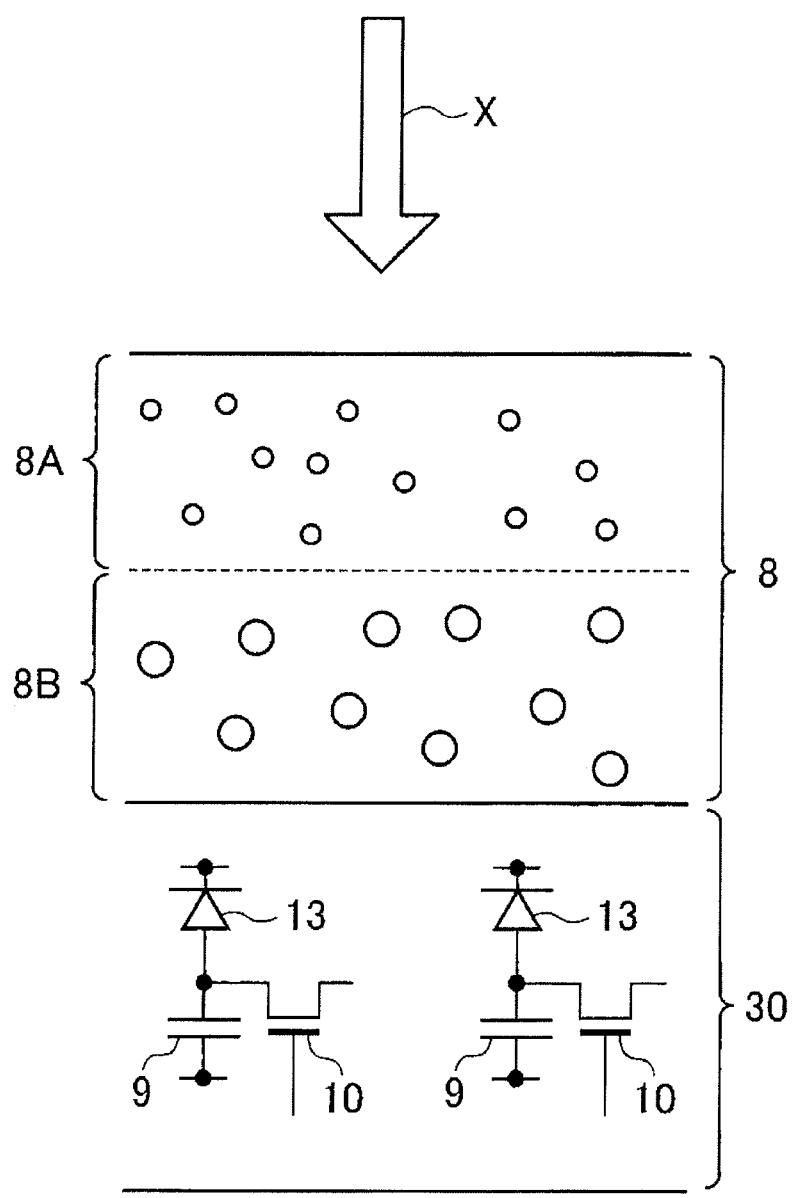
FIG. 9 is a schematic view showing a multilayer structure of small particles and large particles in a scintillator.

Further, the scintillator 8 may be given a multilayer structure of small particles and large particles. For example, as shown in FIG. 9, configuring the scintillator 8 in such a way that its irradiated side is a region 8A of small particles and its TFT substrate 30 side is a region 8B of large particles results in less image blur, but it is difficult for diagonal sections of the light emitted radially by the small particles to reach the TFT substrate 30 and sensitivity decreases. Further, by changing the ratio of the region 8A and the region 8B to increase the layer of large particles with respect to the layer of small particles, the sensitivity of the scintillator 8 becomes higher, but light scattering affects the adjacent pixels, so image quality deteriorates.

Further, the higher the fill rate is, the higher the sensitivity of the scintillator 8 becomes, but light scattering increases and image quality deteriorates. Here, the fill rate is a value equal to the total volume of the particles of the scintillator 8 divided by the volume of the scintillator 8 multiplied by 100. In the scintillator 8, it is preferred that the fill rate be 50 to 80% by volume because it becomes difficult in terms of manufacture to handle powder when the fill rate exceeds 80%.

Further, the light emission characteristic of the scintillator 8 changes also depending on the doping amount of an activator, so there is a tendency for the light emission amount to increase the greater the doping amount of the activator becomes, but light scattering increases and image quality deteriorates.

Further, by changing the material used for the scintillator 8, the light emission characteristic with respect to radiation becomes different.

For example, by forming the scintillator 8A using GOS and forming the scintillator 8B using CsI(Tl), the scintillator 8A comes to have a sensitivity emphasis and the scintillator 8B comes to have an image quality emphasis.

Further, by giving the scintillator 8 a flat plate or column separation layer structure, the light emission characteristic with respect to radiation becomes different.

For example, by giving the scintillator 8A a flat plate layer structure and giving the scintillator 8B a column separation layer structure, the scintillator 8A comes to have a sensitivity emphasis and the scintillator 8B comes to have an image quality emphasis.

Figure 10:
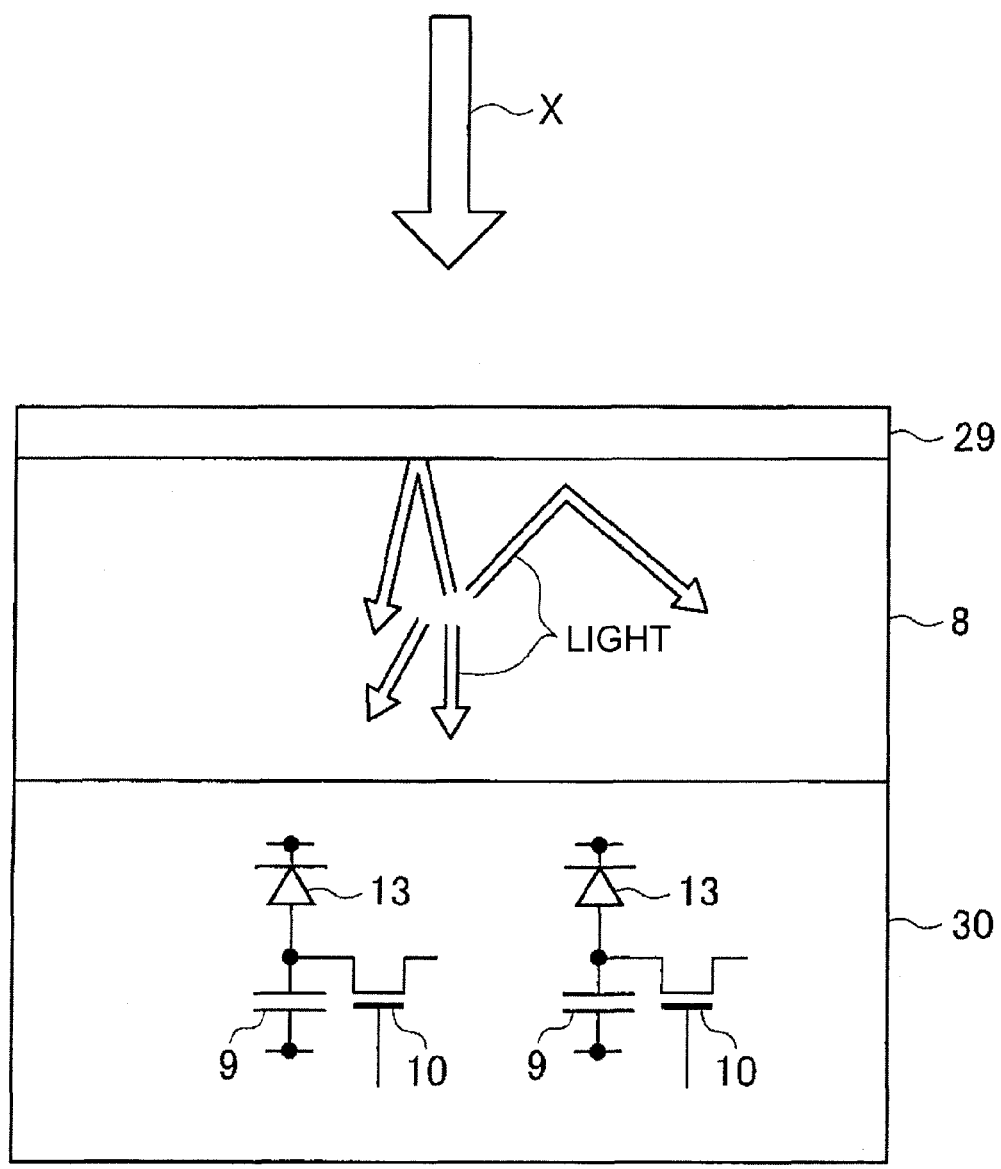
FIG. 10 is a cross-sectional view showing a configuration in a case where a reflective layer is formed on the side of the scintillator on the opposite side of a TFT substrate.

Further, as shown in FIG. 10, by forming a reflective layer 29 that allows X-rays to pass through and reflects visible light on the side of the scintillator 8 on the opposite side of the TFT substrate 30, the generated light may be more efficiently guided to the TFT substrate 30, so sensitivity improves. The method of disposing the reflective layer may be any of sputtering, deposition, and coating. As the reflective layer 29, a material whose reflectivity is high in the emission wavelength region of the scintillator 8 that is used, such as Au, Ag, Cu, Al, Ni, or Ti, is preferred. For example, in a case where the scintillator 8 comprises GOS:Tb, then a material such as Ag, Al, or Cu, whose reflectivity is high in the wavelength region of 400 nm to 600 nm, is preferable; as for the thickness of the reflective layer 29, reflectivity is not obtained with a thickness less than 0.01 μm, and further effects are not obtained in terms of improvements in reflectivity even if the thickness exceeds 3 μm, so 0.01 μm to 3 μm is preferred.

Here, it goes without saying that the scintillator 8 may have its characteristic made different by combining and performing a change to, the particle diameter of the particles, the multilayer structure of the particles, the fill rate of the particles, the doping amount of the activator, the material, and the layer structure and the formation of the reflective layer 29.

Further, the light reception characteristics of the TFT substrates 30A and 30B with respect to light may be changed by, changing the material of the photoelectric conversion film 4, or forming a filter between the TFT substrate 30A and the scintillator 8A and between the TFT substrate 30B and the scintillator 8B, or changing the light-receiving area of the sensor portions 13 between the TFT substrate 30A and the TFT substrate 30B to make the light-receiving area wider on the side with the sensitivity emphasis than on the side with the image quality emphasis, or changing the pixel pitch between the TFT substrate 30A and the TFT substrate 30B to make the pixel pitch narrower on the side with the image quality emphasis than on the side with the sensitivity emphasis, or changing the signal read-out characteristics of the TFT substrates 30A and 30B.

In the present exemplary embodiment, the characteristics of the radiographic images imaged by the radiation detectors 20A and 20B are made different by changing the thickness of the scintillators 8A and 8B, the particle diameter of the particles, the multilayer structure of the particles, the fill rate of the particles, the doping amount of the activator, the material, and the layer structure, or forming the reflective layer 29, or forming a filter between the TFT substrate 30A and the scintillator 8A and between the TFT substrate 30B and the scintillator 8B, or changing the light-receiving area of the sensor portions 13 between the TFT substrate 30A and the TFT substrate 30B to make the light-receiving area wider on the side with the sensitivity emphasis than on the side with the image quality emphasis, or changing the pixel pitch between the TFT substrate 30A and the TFT substrate 30B to make the pixel pitch narrower on the side with the image quality emphasis than on the side with the sensitivity emphasis.

Specifically, the radiation detector 20A is given an image quality emphasis and the radiation detector 20B is given a sensitivity emphasis.

Next, the configuration of an electronic cassette 40 into which the imaging section 21 is built in will be described.

Figure 11:
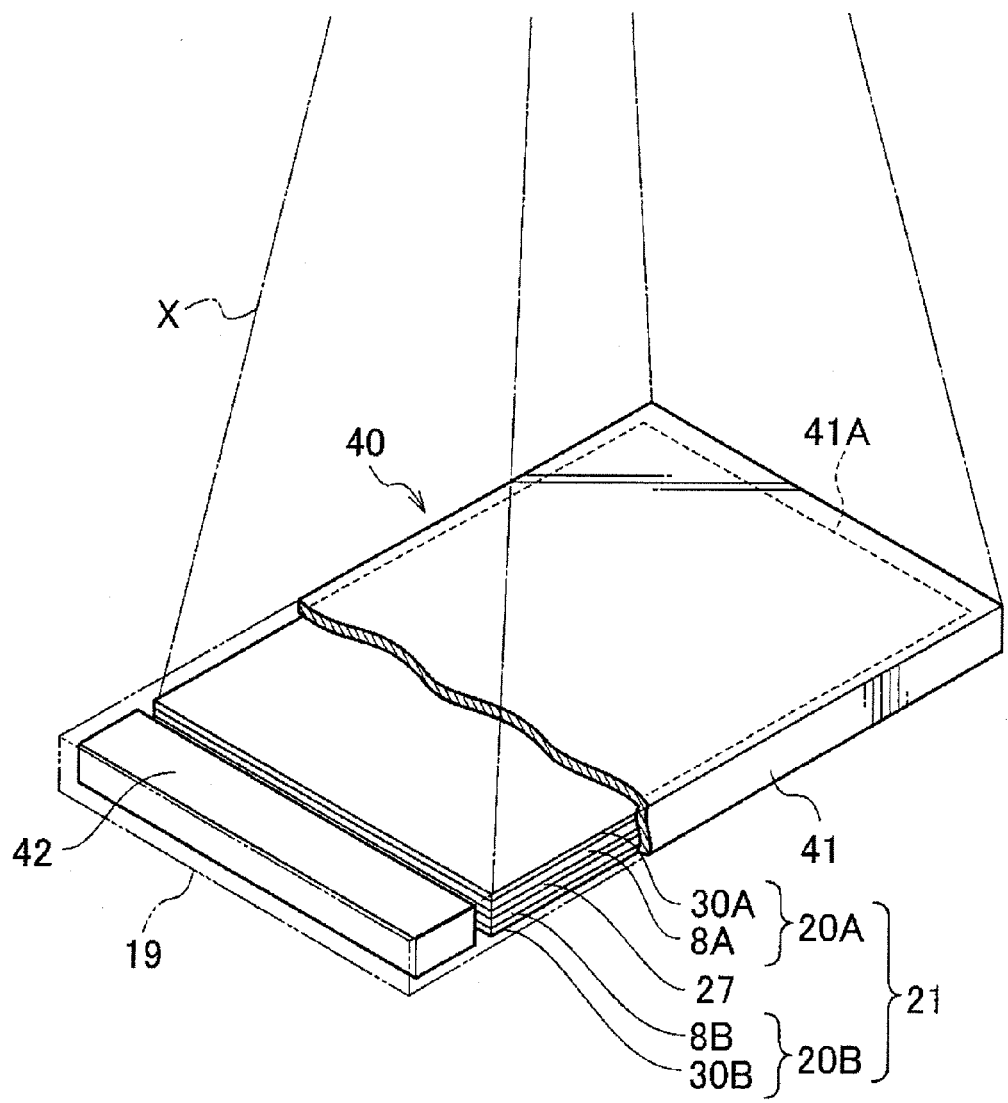
FIG. 11 is a perspective view showing the configuration of an electronic cassette according to the second exemplary embodiment.
Figure 12:
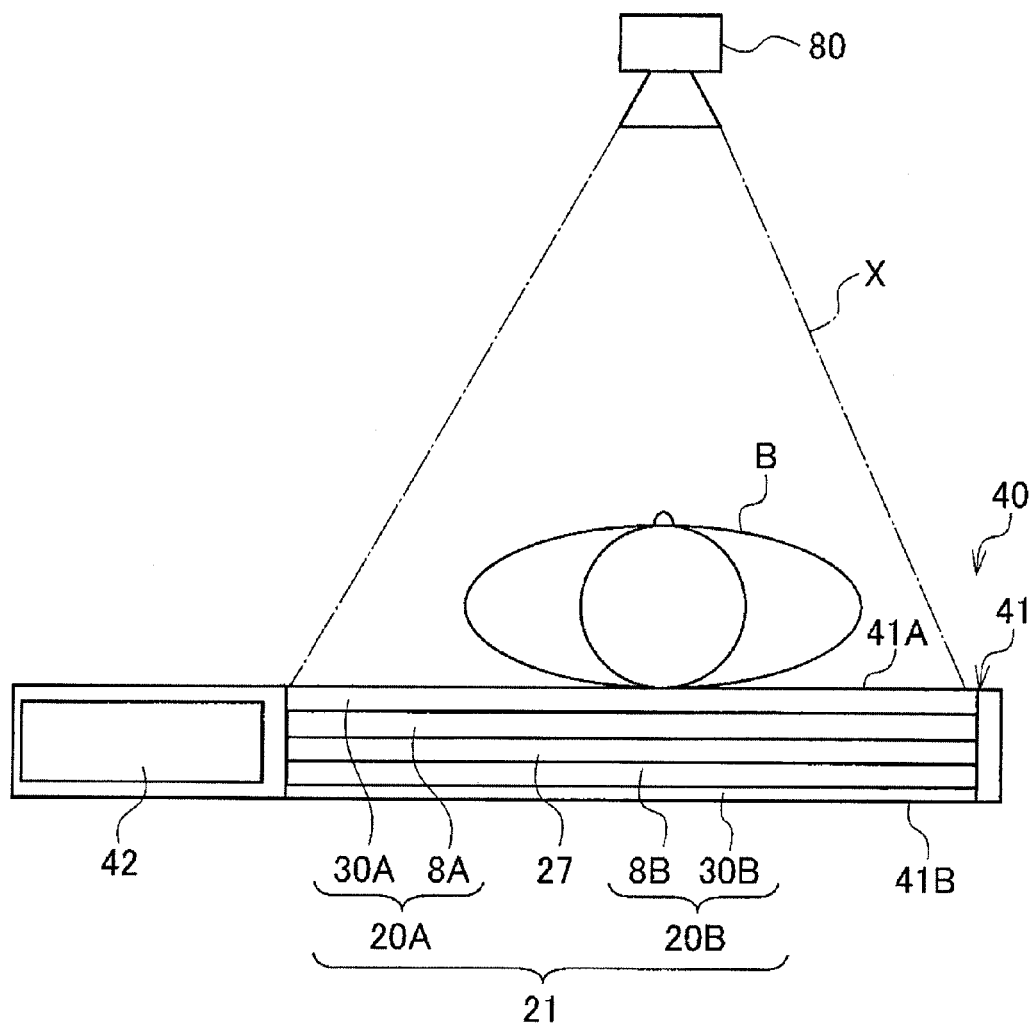
FIG. 12 is a cross-sectional view showing the configuration of the electronic cassette according to the second exemplary embodiment.

In FIG. 11, there is shown a perspective view showing the configuration of the electronic cassette 40, and in FIG. 12, there is shown a cross-sectional view of the electronic cassette 40.

The imaging section 21 is disposed inside the casing 41 of the electronic cassette 40. In the casing 41, regions corresponding to the disposed position of the imaging section 21 on one side and on the other side of the flat plate shape serve as imaging regions 41A and 41B to which radiation is irradiated at the time of imaging. As shown in FIG. 12, the imaging section 21 is built in the casing 41 so that the radiation detector 20A is on the imaging region 41A side of the light-blocking plate 27; the imaging region 41A is an imaging region with an image quality emphasis and the imaging region 41B is an imaging region with a sensitivity emphasis.

Figure 13:
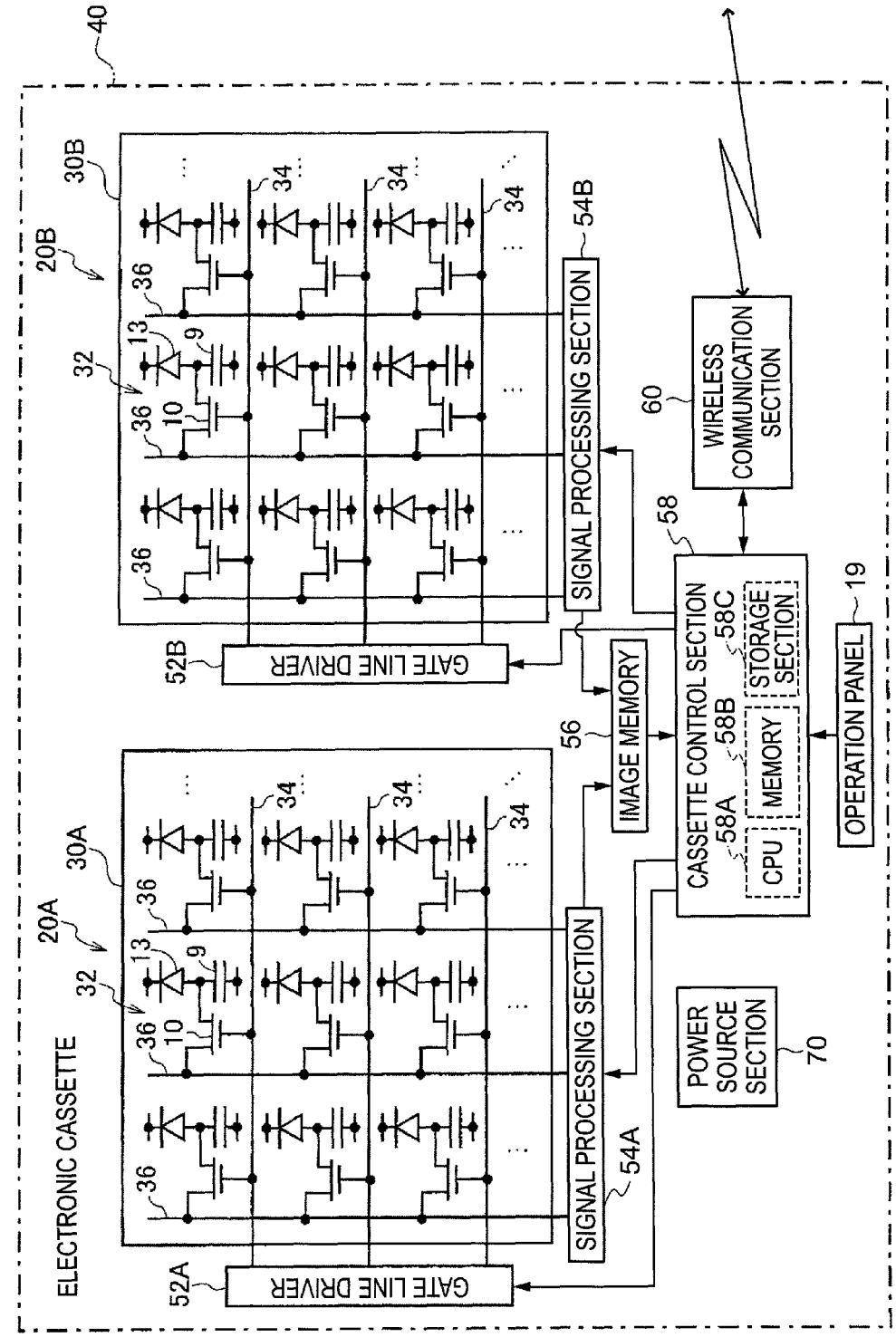
FIG. 13 is a block diagram showing the configurations of main sections of an electrical system of the electronic cassette according to the second exemplary embodiment.

In FIG. 13, there is shown a block diagram showing the configurations of main sections of an electrical system of the electronic cassette 40 according to the present exemplary embodiment.

In the radiation detectors 20A and 20B, a gate line driver 52 is positioned on one side of two sides adjacent to each other, and a signal processing section 54 is positioned on the other side. Below, in the case of distinguishing between the gate line drivers 52 and the signal processing sections 54 disposed in correspondence to the two radiation detectors 20A and 20B, the letter A will be added to the gate line driver 52 and the signal processing section 54 corresponding to the radiation detector 20A and the letter B will be added to the gate line driver 52 and the signal processing section 54 corresponding to the radiation detector 20B.

The individual gate lines 34 of the TFT substrate 30A are connected to the gate line driver 52A, the individual data lines 36 of the TFT substrate 30A are connected to the signal processing section 54A, the individual gate lines 34 of the TFT substrate 30B are connected to the gate line driver 52B, and the individual data lines 36 of the TFT substrate 30B are connected to the signal processing section 54B.

The thin-film transistors 10 of the TFT substrates 30A and 30B are sequentially switched ON in row units by signals supplied via the gate lines 34 from the gate line drivers 52A and 52B, and the electric charges that have been read out by the thin-film transistors 10 switched to ON-state are transmitted through the data lines 36 as electrical signals and are input to the signal processing sections 54A and 54B. Because of this, the electric charges are sequentially read out in row units, and two-dimensional radiographic images become acquirable.

An image memory 56 is connected to the signal processing sections 54A and 54B, and the image data that have been output from A/D converters of the signal processing sections 54A and 54B are sequentially stored in the image memory 56.

The cassette control section 58 individually controls the operations of the gate line drivers 52A and 52B and may individually control the reading-out of the image information representing the radiographic images from the TFT substrates 30A and 30B.

Next, the operations of the electronic cassette 40 according to the present exemplary embodiment will be described.

When imaging a radiographic image, the electronic cassette 40 according to the present exemplary embodiment may perform imaging using only either one of the radiation detectors 20A and 20B, or may perform imaging using both of the radiation detectors 20A and 20B.

Further, when performing imaging using both of the radiation detectors 20A and 20B, the electronic cassette 40 may generate an energy subtraction image by performing image processing that performs weighted addition, per corresponding pixel, of the radiographic images imaged by the radiation detectors 20A and 20B.

The imaging region 41A with the image quality emphasis and the imaging region 41B with the sensitivity emphasis are disposed in the electronic cassette 40, and by reversing the entire electronic cassette 40, the electronic cassette 40 may image a radiographic image with the imaging region 41A or the imaging region 41B.

The electronic cassette 40 is positioned so that, as shown in FIG. 12, it is spaced apart from a radiation generator 80 that generates radiation, with the imaging region 41A face-up in the case of performing imaging with the image quality emphasis and imaging the energy subtraction image and with the imaging region 41B face-up in the case of performing imaging with the sensitivity emphasis, and an imaging target site B of a patient is positioned on the imaging region. The radiation generator 80 emits a dose of radiation corresponding to imaging conditions and so forth given beforehand. The radiation X emitted from the radiation generator 80 carries image information as a result of passing through the imaging target site B and is thereafter irradiated to the electronic cassette 40.

The radiation X irradiated from the radiation generator 80 passes through the imaging target site B and thereafter reaches the electronic cassette 40. Because of this, electric charges corresponding to the dose of the irradiated radiation X are generated in the sensor portions 13 of the radiation detector 20 built in the electronic cassette 40, and the electric charges generated in the sensor portions 13 are stored in the capacitors 9.

The cassette control section 58 controls the operations of the gate line drivers 52A and 52B and receives, via the wireless communication section 60 from the console, imaging condition information indicating whether to perform imaging with an image quality emphasis, to perform imaging with a sensitivity emphasis, or to image an energy subtraction image during the imaging. Additionally, after the application of the radiation X ends, the cassette control section 58 controls the gate line drivers 52A and 52B to perform image read-out in accordance with the imaging condition information.

In this way, by reversing the body of the electronic cassette 40 and performing imaging with the imaging region 41A or the imaging region 41B, the electronic cassette 40 may easily image radiographic images with different characteristics. Further, the electronic cassette 40 may also image an energy subtraction image.

Further, as shown in FIG. 12, the radiation detectors 20A and 20B are built in the electronic cassette 40 according to the present exemplary embodiment, so that the radiation detector 20A is back-side irradiated with respect to the imaging region 41A and the radiation detector 20B is back-side irradiated with respect to the imaging region 41B, but even in a case where the radiation passes through the TFT substrates 30, the amount of radiation absorbed by the substrates 1 is small, so a drop in sensitivity with respect to the radiation X may be suppressed.

The present invention has been described above using the exemplary embodiments. However, the technical scope of the present invention is not limited to the scope described in the above exemplary embodiments. A variety of changes or improvements may be made to the above exemplary embodiments without departing from the gist of the invention, and the technical scope of the present invention also includes embodiments to which such changes or improvements have been made.

Further, the above exemplary embodiments are not intended to limit the inventions according to the claims, and it is not the case that all combinations of features described in the exemplary embodiments are essential to the invention. The above exemplary embodiments include inventions of a variety of stages, and a variety of inventions may be extracted by appropriate combinations of the plural configural requirements disclosed. Even when several configural requirements are omitted from all the configural requirements described in the exemplary embodiments, configurations from which those several configural requirements have been omitted may also be extracted as inventions as long as effects are obtained.

In the above exemplary embodiments, a case was described where the present invention was applied to the electronic cassette 40 that is a portable radiographic imaging device. However, the present invention is not limited to this. The present invention may also be applied to a stationary radiographic imaging device.

Figure 14:
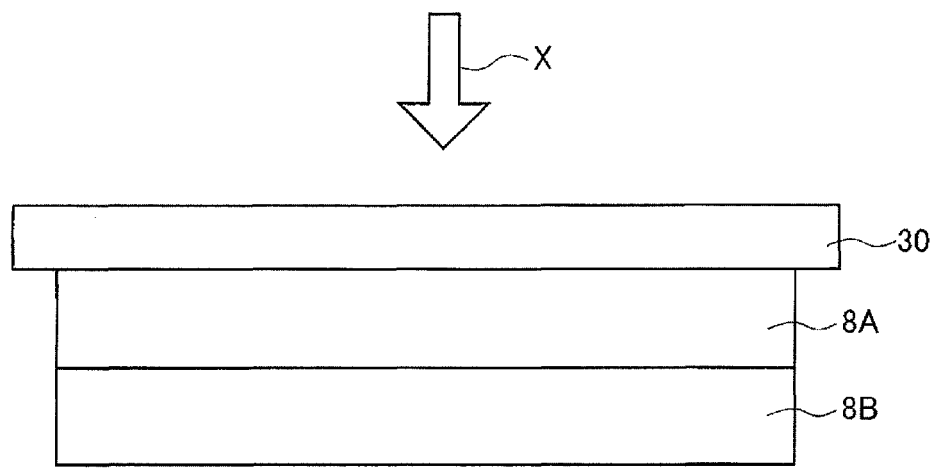
FIG. 14 is a cross-sectional view showing the configuration of a radiation detector according to another exemplary embodiment.
Figure 15:
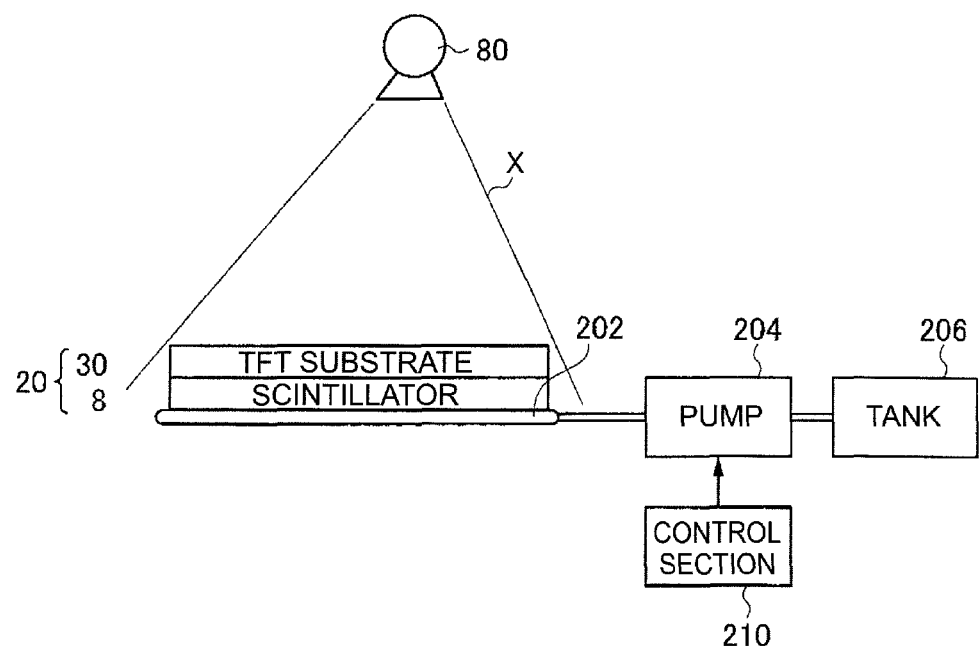
FIG. 15 is a side view showing the schematic configuration of a radiographic imaging device according to another exemplary embodiment.

Further, in the above exemplary embodiments, a case was described where one scintillator 8 was disposed on the TFT substrate 30. However, the present invention is not limited to this. For example, as shown in FIG. 14, plural (two in FIG. 14) scintillators 8 (8A and 8B) may also be disposed on the TFT substrate 30. Further, sensitivity and image quality characteristics change depending on the thickness of the scintillator 8, so as shown in FIG. 15, a bag body 202 having optical transparency may be positioned so as to oppose the detection region of the radiation detector 20, and injection of a liquid scintillator into the bag body 202 from a tank 206 in which the liquid scintillator is stored and extraction of the liquid scintillator injected into the bag body 202 may be performed by a pump 204, and the thickness of the bag body 202 may be changed by changing the fluid volume of the liquid scintillator stored inside the bag body 202. Because of this, the sensitivity and image quality characteristics of the radiographic image to be imaged may be changed. The bag body 202 may also be positioned on the TFT substrate 30 instead of the scintillator 8, and the injection of the liquid scintillator into the bag body 202 and the extraction of the liquid scintillator injected into the bag body 202 may be performed by the pump 204. By using the pump 204 to fill the bag body 202 with the liquid scintillator and let the liquid scintillator out of the bag body 202, the bag body 202 may be brought into close contact with and separated from the TFT substrate 30, so when the TFT substrate 30 has become deteriorated by radiation, for example, just the TFT substrate 30 may be repositioned.

Further, in the first exemplary embodiment, a case was described where the cassette control section 58 and the power source section 70 were positioned inside the casing 41 of the electronic cassette 40 so as to not overlap with the case 42 and the radiation detector 20. However, the present invention is not limited to this. For example, the cassette control section 58 and the power source section 70 may also be positioned so as to overlap with the radiation detector 20.

Figure 16:
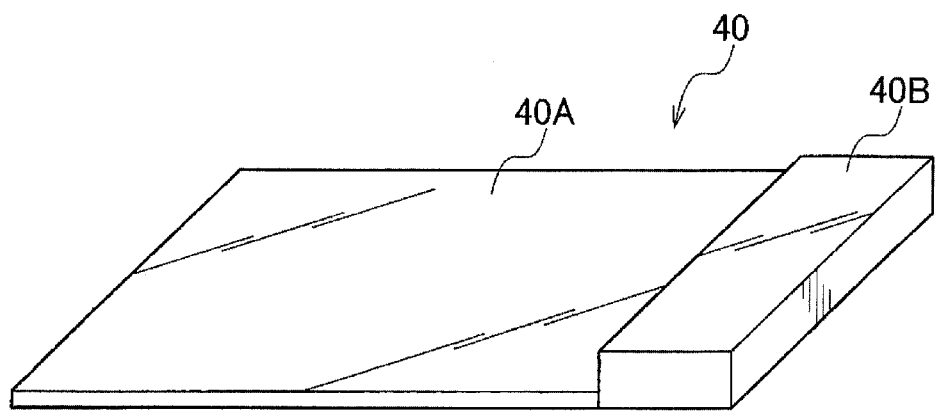
FIG. 16 is a perspective view showing the configuration of an electronic cassette according to another exemplary embodiment.

Further, in the above exemplary embodiments, a case was described where the electronic cassette 40 was formed in a flat plate rectangular shape and with a substantially constant thickness. However, the present invention is not limited to this. For example, as shown in FIG. 16, an imaging section 40A into which the radiation detector 20 is built in may also be formed thinner than a control section 40B in which the cassette control section 58 and the power source section 70 are positioned.

Figure 17:
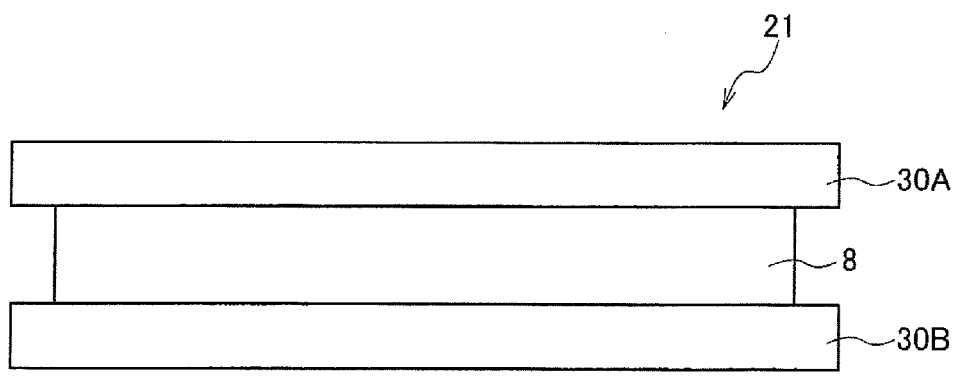
FIG. 17 is a cross-sectional view showing the configuration of an imaging section according to another exemplary embodiment.
Figure 18:
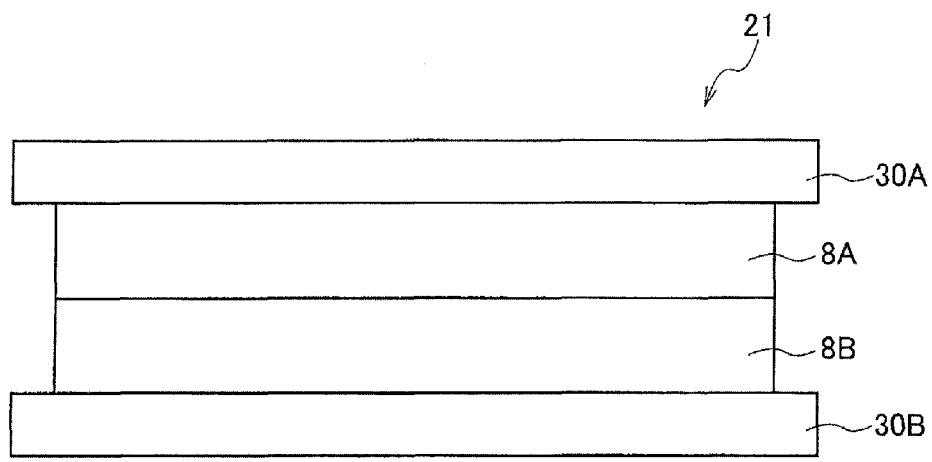
FIG. 18 is a cross-sectional view showing the configuration of an imaging section according to another exemplary embodiment.
Figure 19:
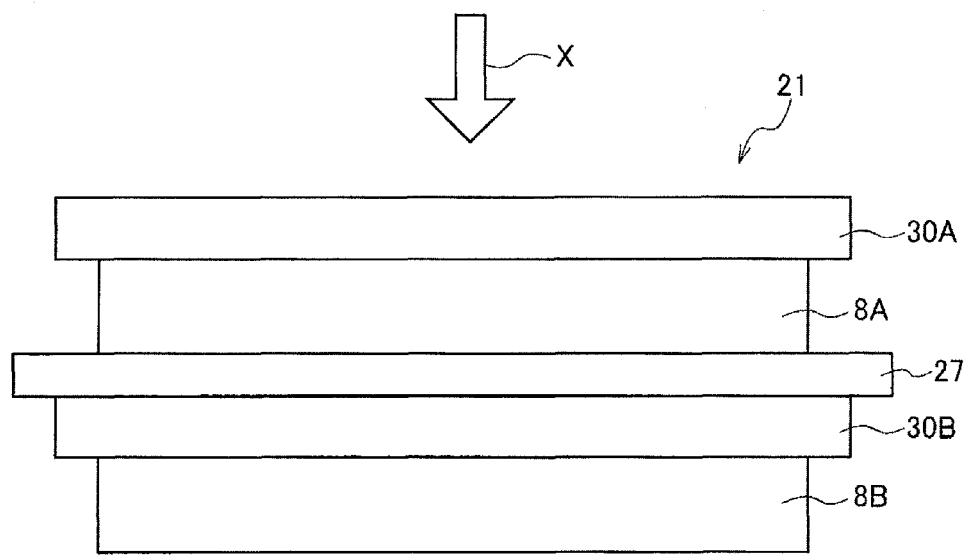
FIG. 19 is a cross-sectional view showing the configuration of an imaging section according to another exemplary embodiment.
Figure 20:
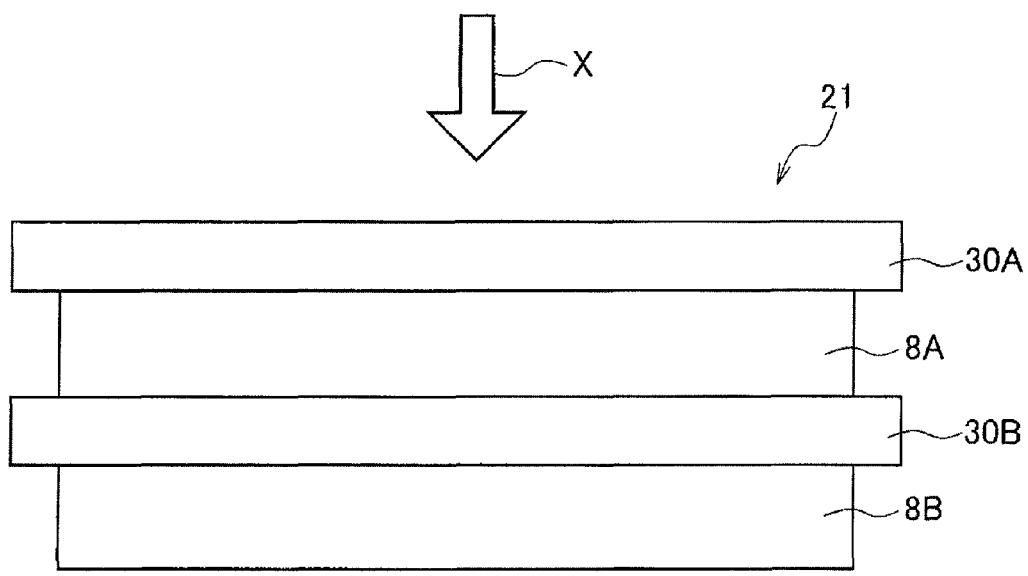
FIG. 20 is a cross-sectional view showing the configuration of an imaging section according to another exemplary embodiment.

Further, in the second exemplary embodiment, a case was described where the imaging section 21 was given a configuration in which the two radiation detectors 20A and 20B were positioned in such a way that their scintillator 8 sides opposed each other with the light-blocking plate 27 in between. However, the present invention is not limited to this. For example, as shown in FIG. 17, the imaging section 21 may also be given a configuration in which the TFT substrate 30A is positioned on one side of one scintillator 8 and the TFT substrate 30B is positioned on the other side of the scintillator 8. Further, in a case where the radiation detectors 20A and 20B are little affected by the light of one scintillator 8 on the other, as shown in FIG. 18, the imaging section 21 may also be given a configuration in which the light-blocking plate 27 is not disposed and the radiation detectors 20A and 20B are positioned in such a way that the scintillators 8A and 8B face each other. Further, in a case where the electronic cassette 40 images an energy subtraction image, as shown in FIG. 19, the radiation detectors 20A and 20B may also be layered in such a way that they become back-side irradiated with respect to the radiation X with the light-blocking plate 27 in between, and as shown in FIG. 20, the radiation detectors 20A and 20B may also be layered in such a way that they become back-side irradiated with respect to the radiation X without the light-blocking plate 27 being disposed.

Figure 21:
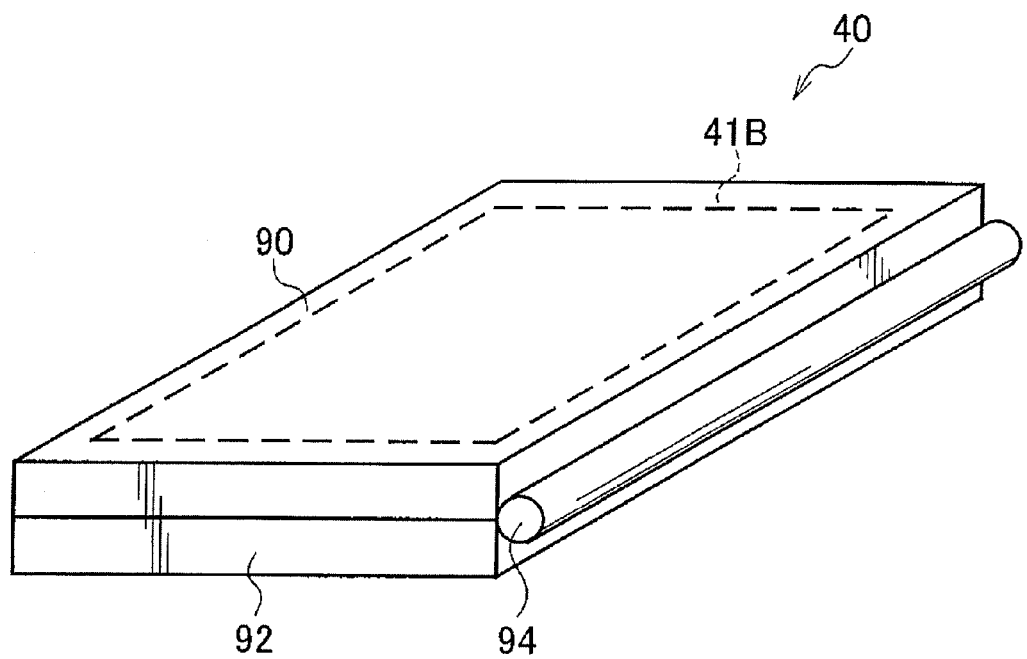
FIG. 21 is a perspective view showing the configuration of an electronic cassette that may be opened and closed, according to another exemplary embodiment.
Figure 22:
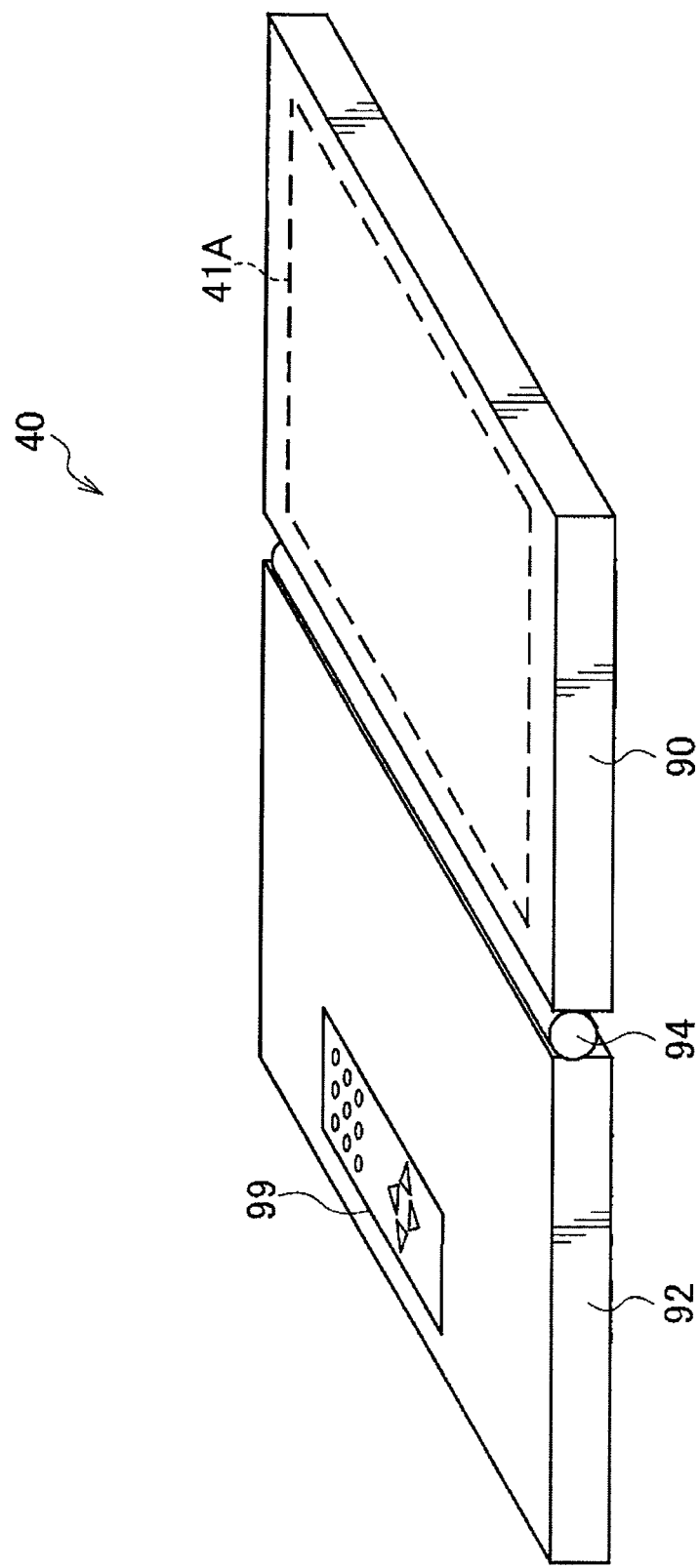
FIG. 22 is a perspective view showing the configuration of the electronic cassette that may be opened and closed, according to the other exemplary embodiment.
Figure 23:
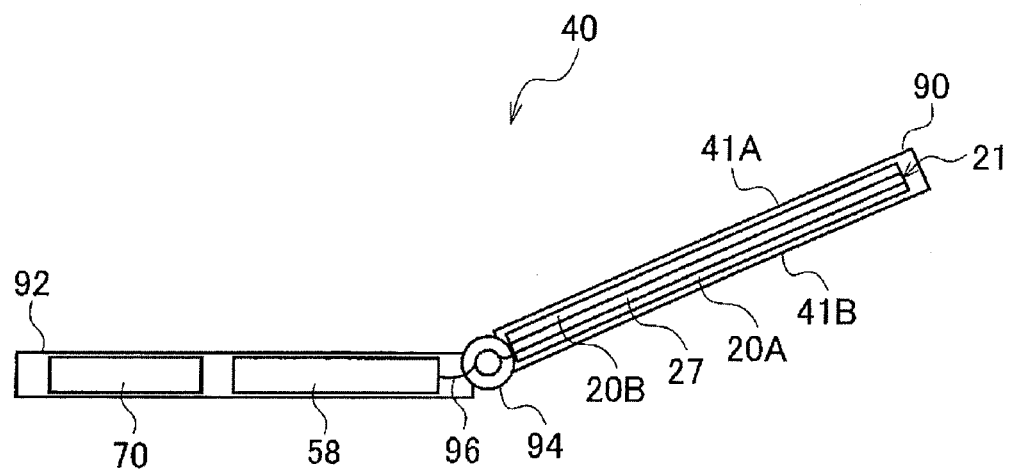
FIG. 23 is a cross-sectional view showing the configuration of the electronic cassette that may be opened and closed, according to the other exemplary embodiment.
Figure 24:
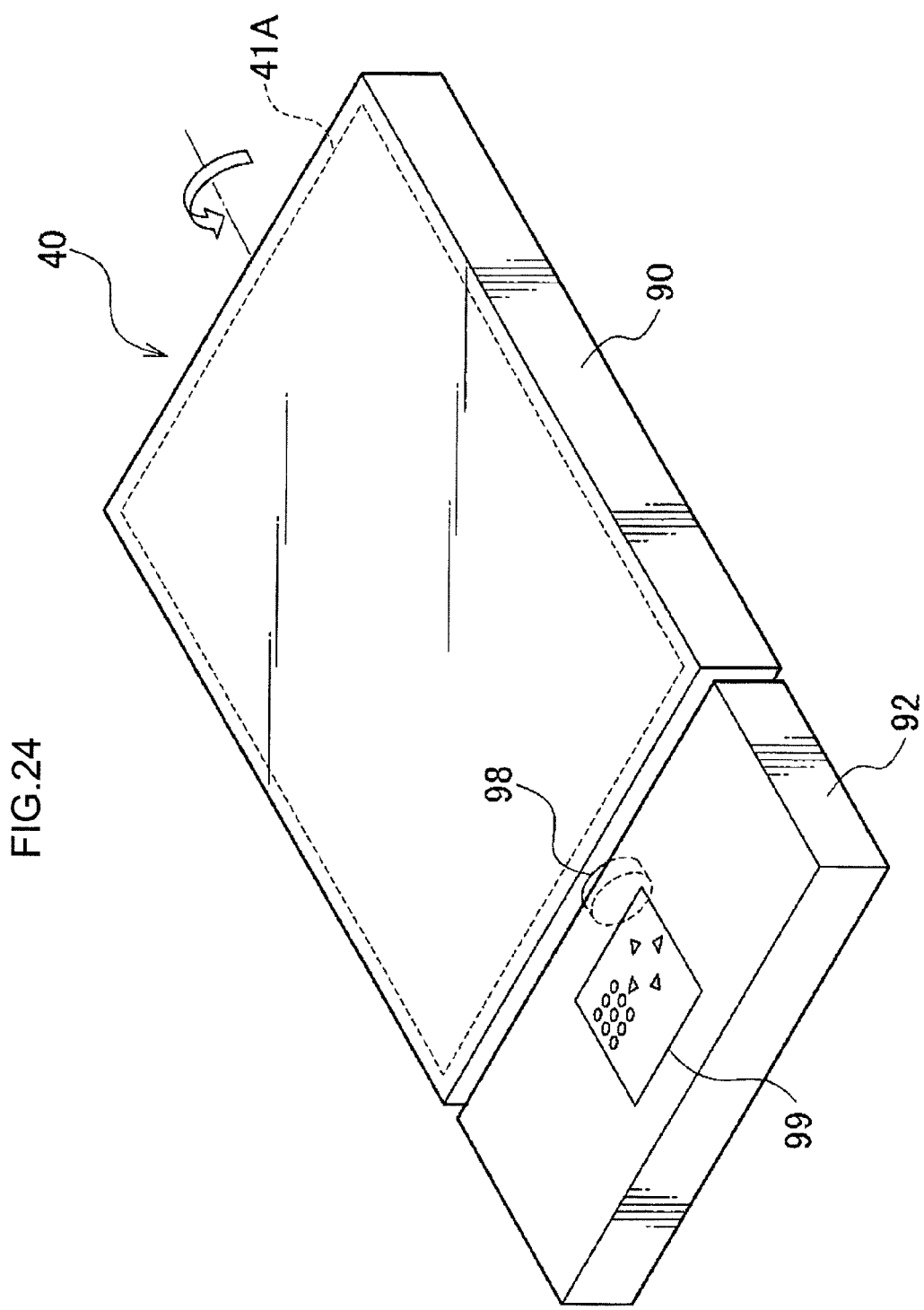
FIG. 24 is a perspective view showing the configuration of an electronic cassette that may be reversed, according to another exemplary embodiment.
Figure 25:
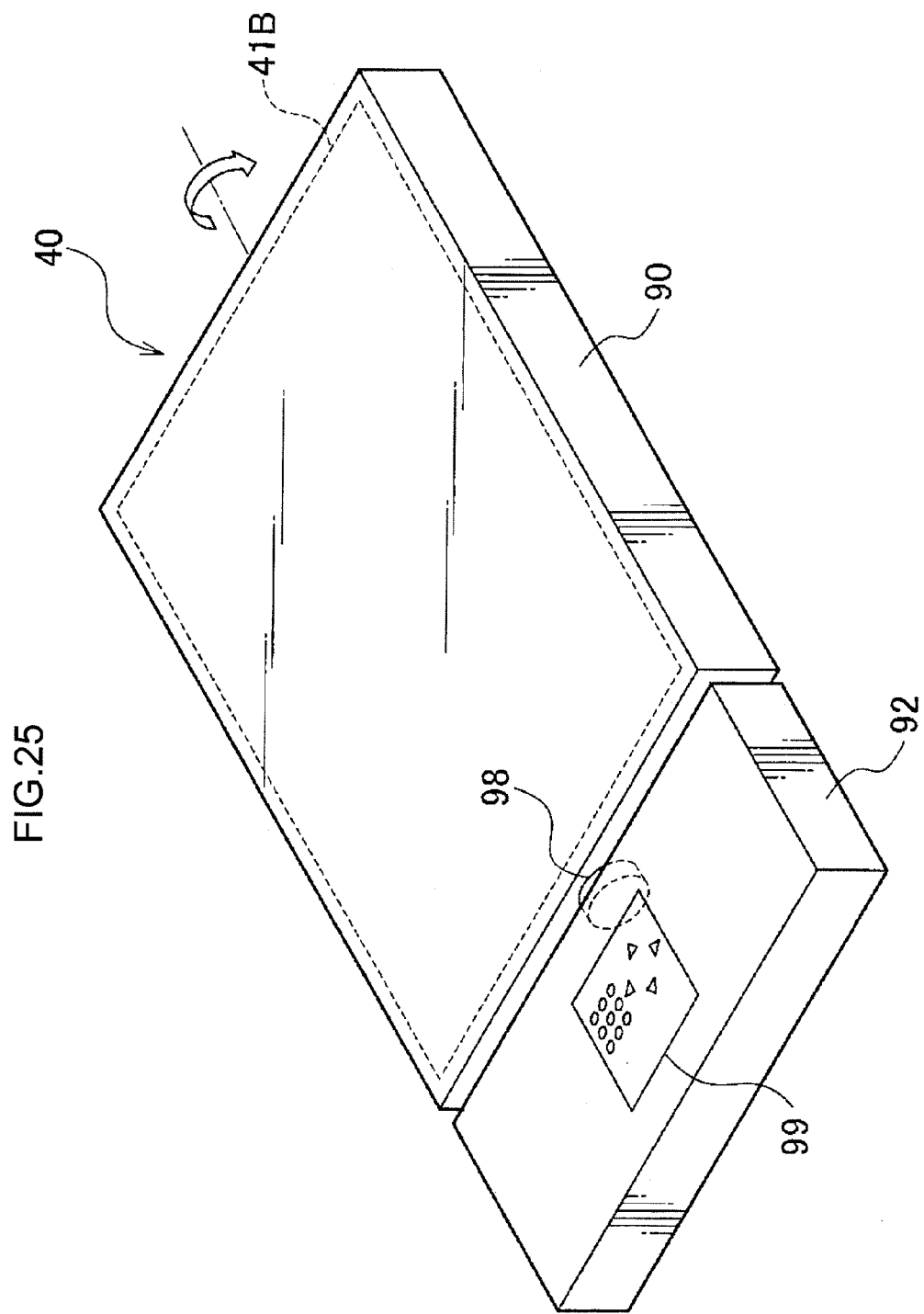
FIG. 25 is a perspective view showing the configuration of the electronic cassette that may be reversed, according to the other exemplary embodiment.
Figure 26:
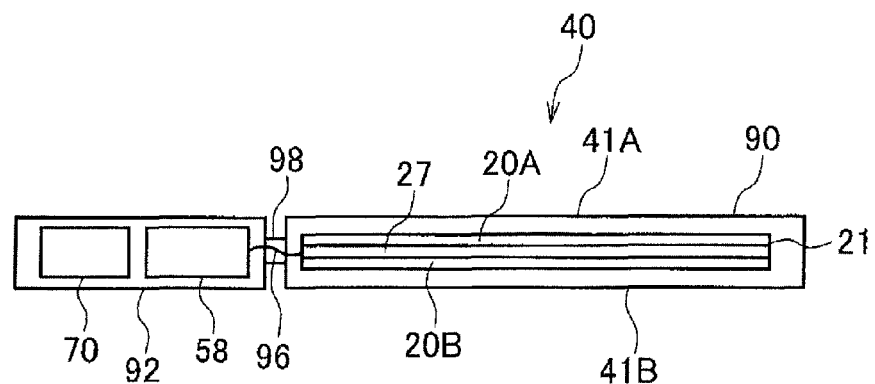
FIG. 26 is a cross-sectional view showing the configuration of the electronic cassette that may be reversed, according to the other exemplary embodiment.

Further, in the second exemplary embodiment, the entire electronic cassette 40 may be reversed so that imaging with both sides of the imaging region 41A and the imaging region 41B may be performed, but a configuration that makes it possible to open and close the electronic cassette 40, such as shown in FIG. 21 to FIG. 23, and a configuration that makes it possible to reverse part of the electronic cassette 40, such as shown in FIG. 24 to FIG. 26, may be exemplified.

In FIG. 21 and FIG. 22, there are shown perspective views showing other another configuration of the electronic cassette 40, and in FIG. 23, there is shown a cross-sectional view showing the schematic configuration of the electronic cassette 40. Identical reference signs will be given to sections corresponding to those of the electronic cassette 40 of the second exemplary embodiment, and description of sections having the same functions will be omitted.

The imaging section 21, the gate line drivers 52A and 52B, and the signal processing sections 54A and 54B are built in the electronic cassette 40, and a flat plate-shaped imaging unit 90, which images radiographic images resulting from irradiated radiation, and a control unit 92, into which the cassette control section 58 and the power source section 70 are built in, are coupled together by a hinge 94 in such a way that the imaging unit 90 and the control unit 92 may be opened and closed.

When one of the imaging unit 90 and the control unit 92 rotates about the hinge 94 with respect to the other, the imaging unit 90 and the control unit 92 may be opened to a deployed state in which the imaging unit 90 and the control unit 92 lie side by side (FIG. 22) and closed to a stored state in which the imaging unit 90 and the control unit 92 are folded on top of each other (FIG. 21).

The imaging section 21 is built in the imaging unit 90 in such a way that, as shown in FIG. 23, in the stored state the radiation detector 20B is on the control unit 92 side and the radiation detector 20A is on the outside (the opposite side of the control unit 92 side). The side of the imaging unit 90 that becomes the outside in the stored state is the imaging region 41B with the sensitivity emphasis, and the side of the imaging unit 90 that opposes the control unit 92 is the imaging region 41A with the image quality emphasis.

The imaging section 21 is connected to the cassette control section 58 and the power source section 70 by a connection wire 96 disposed in the hinge 94.

In this way, the electronic cassette 40 is opened and closed and performs imaging with the imaging region 41A or the imaging region 41B. Because of this, the electronic cassette 40 may easily image radiographic images with different characteristics.

In FIG. 24 and FIG. 25, there are shown perspective views showing another configuration of the electronic cassette 40 according to the exemplary embodiments, and in FIG. 26, there is shown a cross-sectional view showing the schematic configuration of the electronic cassette 40. Identical reference signs will be given to sections corresponding to those of the electronic cassette 40 of the second exemplary embodiment, and description of sections having the same functions will be omitted.

The imaging section 21, the gate line drivers 52A and 52B, and the signal processing sections 54A and 54B are built in the electronic cassette 40, and a flat plate-shaped imaging unit 90, which images radiographic images resulting from irradiated radiation, and a control unit 92, into which the cassette control section 58 and the power source section 70 are built, are coupled together by a rotating shaft 98 in such a way that the imaging unit 90 and the control unit 92 may be rotated.

Further, in the imaging unit 90, the imaging regions 41A and 41B are disposed on one side and the other side of the flat plate shape in correspondence to the disposed position of the imaging section 21.

The imaging section 21 is built into the imaging unit 90 in such a way that the radiation detector 20B is on the imaging region 41B side and the radiation detector 20A is on the imaging region 41A side. The imaging section 21 is configured in such a way that the imaging region 41B is the imaging region with the sensitivity emphasis and the imaging region 41A is the imaging region with the image quality emphasis.

The imaging section 21 is connected to the cassette control section 58 and the power source section 70 by a connection wire 96 disposed in the rotating shaft 98.

When one of the imaging unit 90 and the control unit 92 rotates with respect to the other, the imaging unit 90 and the control unit 92 may be changed to a state in which the imaging region 41A and an operation panel 99 lie side by side (FIG. 24) and a state in which the imaging region 41B and the operation panel 99 lie side by side (FIG. 25).

In this way, the electronic cassette 40 is rotated and performs imaging with the imaging region 41A or the imaging region 41B, whereby the electronic cassette 40 may easily image radiographic images with different characteristics.

Further, as the sensor portions 13 of the radiation detector 20, organic CMOS sensors in which the photoelectric conversion film 4 is configured by a material including an organic photoelectric conversion material may also be used, and as the TFT substrate of the radiation detector 20, an organic TFT array sheet in which organic transistors including an organic material as the thin-film transistors 10 are arrayed on a flexible sheet may also be used. The organic CMOS sensors are disclosed in, for example, JP-A No. 2009-212377. Further, the organic TFT array sheet is disclosed in, for example, "The University of Tokyo Develops "Ultra-flexible" Organic Transistor", NIKKEI Newspaper (URL: http://www.nikkei.com/tech/trend/article/g=96958A9C93819499E2EAE2E0E48D-E2EAE3E3E0E2E3E2E2E2E2E2E2E2;p=9694E0E7E2E6-E0E2E3E2E2E0E2E0) (accessed May 8, 2011).

In the case of using CMOS sensors as the sensor portions 13 of the radiation detector 20, there are the advantage that photoelectric conversion may be performed at a high speed and the advantage that, as a result of being able to make the substrate thin, the absorption of radiation may be suppressed in the case of employing the ISS system and the radiation detector may be suitably applied to imaging by mammography.

Examples of defect in the case of using CMOS sensors as the sensor portions 13 of the radiation detector 20 include resistance with respect to radiation being low in the case of using a crystalline silicon substrate. For this reason, conventionally, there has also been the technique of implementing the measure of disposing a fiber optic plate (FOP) between the sensor portions and the TFT substrate.

In view of this defect, the technique of using a silicon carbide (SiC) substrate as a semiconductor substrate whose resistance with respect to radiation is high may be applied. By using a SiC substrate, there are the advantage that it may be used as the ISS system and the advantage that, because SiC has low internal resistance and a small heat emission amount compared to Si, the heat emission amount when imaging moving images may be suppressed and a drop in sensitivity accompanying a rise in the temperature of CsI may be suppressed.

Figure 30:
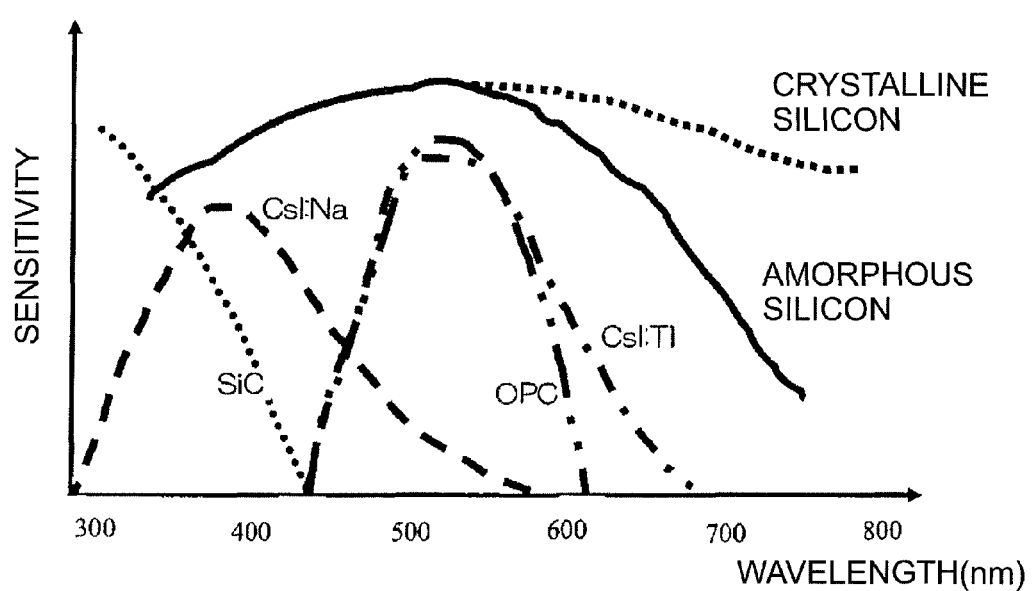
FIG. 30 is a graph showing an example of the sensitivity characteristics of various materials.

In this way, substrates whose resistance with respect to radiation is high, such as SiC substrates, usually are wide gap (to about 3 eV), so as shown in FIG. 30 as an example, the absorption end is about 440 nm corresponding to the blue region. Thus, in this case, a CsI:Tl, GOS, or other scintillator that emits light in the green region may not be used.

Research on these scintillators that emit light in the green region has been actively conducted from the sensitivity characteristic of amorphous silicon, so the demand to use the scintillators is high. For this reason, by configuring the photoelectric conversion film 4 using a material including an organic photoelectric conversion material that absorbs emission light in the green region, a scintillator that emits light in the green region may be used.

In a case where the photoelectric conversion film 4 is configured by a material including an organic photoelectric conversion material and the thin-film transistors 10 are configured using a SiC substrate, the sensitivity wavelength regions of the photoelectric conversion film 4 and the thin-film transistors 10 differ, so the light emitted by the scintillator does not become noise in the thin-film transistors 10.

Further, if SiC and a material including an organic photoelectric conversion material are layered as the photoelectric conversion film 4, the film may also receive emission light in the green region in addition to receiving emission light mainly in the blue region like CsI:Na, and as a result this leads to an improvement in sensitivity. Further, there is virtually no absorption of radiation by the organic photoelectric conversion material, so it may be suitably used in the ISS system.

Note that the reason SiC has a high resistance with respect to radiation is because it is difficult for the nuclei of the atoms to be knocked out even when radiation strikes them; this is disclosed in, for example, "Development of Semiconductor Element that may be used for a Long Term under High Radiation Environment, such as Space or Atomic Field", Japan Atomic Energy Research Institute (URL: http://wwwjaea.gojp/jaeri/jpn/publish/01/ff/ff36/sic.html) (accessed May 8, 2011).

Further, examples of semiconductor materials other than SiC whose resistance with respect to radiation is high include C (diamond), BN, GaN, AlN, and ZnO. The reasons these light-element semiconductor materials have a high resistance to radiation are attributable to the fact that the energy required for ionization (electron-hole pair formation) is high and their reaction cross-section is small, because they are mainly wide gap semiconductors and the fact that the bonding between their atoms is strong, and it is difficult for atomic displacement production to occur. This is disclosed in, for example, "New Developments in Atomic Electronics", Electro-technical Laboratory (URL: http://www.aist.gojp/ETL/jp/results/bulletin/pdf/62-10to11/kobayashi150.pdf) (accessed May 8, 2011) and "Research Regarding Anti-Radiation Characteristics of The Zinc Oxide Series Electronic Device", Open Joint Research Report of the Wakasa Wan Energy Research Center for 2009, March 2010. Further, the radiation resistance of GaN is disclosed in, for example, "Assessment of Radiation Resistance Characteristic of Gallium Nitride Element", Tohoku University (URL: http://cycgw1.cyric.tohoku.acjp/~sakemi/ws2007/ws/pdf/narita.pdf) (accessed May 8, 2011).

Because GaN has good thermal conductivity for intended uses other than blue LEDs and high insulation resistance, the integration of GaN into integrated circuits is being researched in power-related fields. Further, as for ZnO, LEDs that emit light mainly in the blue to ultraviolet region are being researched.

Figure 31:
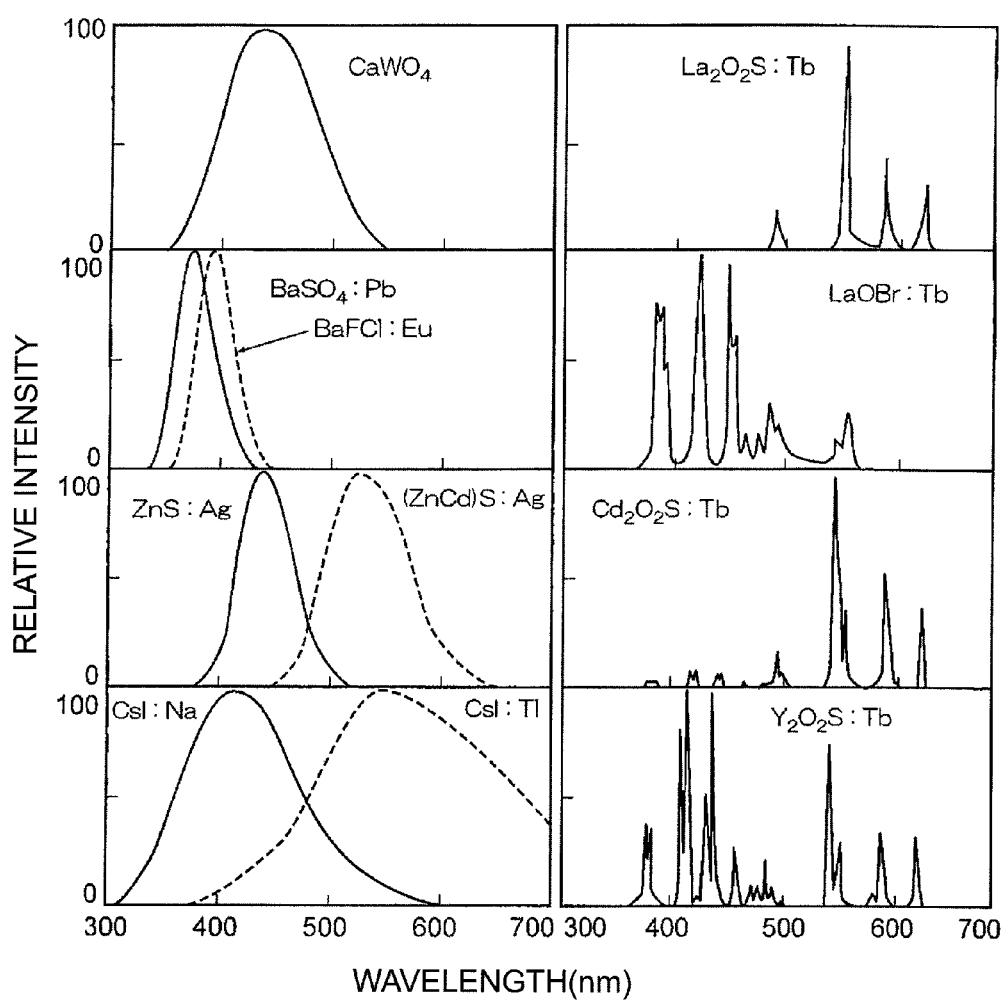
FIG. 31 is a graph showing an example of the sensitivity characteristics of various materials.

Incidentally, in the case of using SiC, the band gap Eg becomes from about 1.1 eV to about 2.8 eV of Si, so the light absorption wavelength λ shifts to the short-wavelength side. Specifically, wavelength λ=1.24/Eg×1000, so the sensitivity changes to a wavelength of about 440 nm. Thus, in the case of using SiC, as shown in FIG. 31 as an example, CsI:Na (peak wavelength: about 420 nm), which emits light in the blue region, is more suitable for the scintillator as the emission wavelength than CsI:Tl (peak wavelength: about 565 nm), which emits light in the green region. As the phosphor, blue emission light is good, so CsI:Na (peak wavelength: about 420 nm), BaFX:Eu (X is a halogen such as Br or I; peak wavelength: about 380 nm) $CaWO_4$ (peak wavelength: about 425 nm), ZnS:Ag (peak wavelength: about 450 nm), LaOBr:Tb, and $Y_2O_2S$:Tb are suitable. In particular, CsI:Na, BaFX:Eu used in CR cassettes and so forth, and $CaWO_4$ used in screens and films are suitably used.

As CMOS sensors whose resistance with respect to radiation is high, CMOS sensors may also be configured by silicon on insulator (SOI) using the configuration of: Si substrate/ thick-film $SiO_2$/organic photoelectric conversion material.

Examples of techniques that may be applied to this configuration include "World First Configuration of Development Bases of High Function Logic Integrated Circuit that has Anti-Radiation Characteristics Achieved by Combination of Leading Edge Consumer SOI Technology and Anti-Radiation Technology for Space", Japan Aerospace Exploration Agency (JAXA), Institute of Space and Astronautical Science (URL: http://wwwjaxajp/press/2010/11/20101122_soi_j.html) (accessed May 8, 2011).

In SOI, the radiation resistance of film thickness SOI is high, so complete separation thick-film SOI and partial separation thick-film SOI are exemplified as high-radiation-durable elements. These SOIs are disclosed in, for example, "Report on an Investigation Regarding The Technological Trend in The Patent Application Regarding SOI (Silicon On Insulator) Technology", Japan Patent Office (URL: http://wwwjpo.gojp/shiryou/pdf/gidou-houkoku/soi.pdf) (accessed May 8, 2011).

Moreover, even in a configuration in which the thin-film transistors 10 etc. of the radiation detector 20 do not have optical transparency (e.g., a configuration in which the active layers 17 are formed by a material that does not have optical transparency, such as amorphous silicon), it is possible to obtain a radiation detector 20 that has optical transparency by placing the thin-film transistors 10 etc. on a substrate 1 that has optical transparency (e.g., a flexible substrate made of synthetic resin) and configuring the section of the substrate 1 where the thin-film transistors 10 etc. are not formed to transmit light. Placing the thin-film transistors 10 etc. that have a configuration that does not have optical transparency on the substrate 1 has optical transparency may be realized by the technique of cutting a microscopic device block created on a first substrate from the first substrate and placing it on a second substrate—specifically, this may be realized by applying fluidic self-assembly (FSA). FSA is disclosed in, for example, "Research of Self-Aligning Placement Technology of Minimal Semiconductor Block", University of Toyama (URL: http://www3.u-toyama.acjp/maezawa/Research/FSA.html) (accessed May 8, 2011).

What is claimed is:

1. A radiographic imaging device comprising: a radiation detector, in which a light-emitting layer that generates light due to irradiation of radiation and a substrate on which plural sensor portions configured including an organic photoelectric conversion material that generates electric charges by receiving light are disposed and are sequentially layered, with the radiation detector being positioned so that radiation that has passed through a subject is made incident from the substrate side.

2. The radiographic imaging device according to claim 1, wherein the substrate is configured by any of plastic resin, an aramid, bio-nanofibers, or a flexible glass substrate.

3. The radiographic imaging device according to claim 1, wherein thin-film transistors, that are configured including an amorphous oxide in their active layers and that read out the electric charges generated in the sensor portions, are formed on the substrate in correspondence to the sensor portions.

4. The radiographic imaging device according to claim 1, wherein the substrate is adhered to an imaging region within a casing, to which the radiation that has passed through the subject is irradiated.

5. The radiographic imaging device according to claim 1, wherein
the light-emitting layer is configured including CsI columnar crystals, and the organic photoelectric conversion material is quinacridone.

6. The radiographic imaging device according to claim 1, further comprising:
- a bag body, disposed so as to overlap with a detection region in which the plural sensor portions of the radiation detector are disposed, in which at least an opposing surface opposing the detection region has an optical transparency;
- a tank that stores a liquid scintillator that emits light when radiation is irradiated; and
- an actuator that performs injection of the liquid scintillator stored in the tank into the bag body and extraction of the liquid scintillator injected into the bag body.

7. The radiographic imaging device according to claim 1, wherein two of the radiation detectors in which the light emission characteristics of the light-emitting layers with respect to radiation differ are positioned to overlap each other.

8. The radiographic imaging device according to claim 7, wherein at least one change to any of the thickness of the light-emitting layers, the particle diameter of particles that fill the light-emitting layers and emit light due to irradiation of radiation, the multilayer structure of the particles, the fill rate of the particles, the doping amount of an activator, the material of the light-emitting layers, the layer structure of the light-emitting layers, or the formation of a reflective layer that reflects the light on the sides of the light-emitting layers not opposing the substrates, is performed on the light-emitting layers of the two radiation detectors.

9. The radiographic imaging device according to claim 1, wherein
- the substrate is further formed with thin-film transistors that read out the electric charges generated in the sensor portions,
- the sensor portions are configured using a wide gap semiconductor substrate,
- the light-emitting layer, the sensor portions, and the thin-film transistors are layered in this order in the radiation detector, and
- the radiation detector is positioned so that the radiation is irradiated from the thin-film transistor side.

* * * * *